(12) United States Patent
Otake

(10) Patent No.: US 6,881,578 B2
(45) Date of Patent: *Apr. 19, 2005

(54) ANALYTE CONCENTRATION DETERMINATION METERS AND METHODS OF USING THE SAME

(75) Inventor: Gary Otake, Union City, CA (US)

(73) Assignee: LifeScan, Inc., Milpitas, CA (US)

(*) Notice: Subject to any disclaimer, the term of this patent is extended or adjusted under 35 U.S.C. 154(b) by 188 days.

This patent is subject to a terminal disclaimer.

(21) Appl. No.: 10/116,386

(22) Filed: Apr. 2, 2002

(65) Prior Publication Data

US 2003/0185705 A1 Oct. 2, 2003

(51) Int. Cl.[7] .............................................. G01N 33/48
(52) U.S. Cl. .................... 436/44; 436/150; 436/169; 436/808; 422/58; 422/61; 422/68.1; 422/82.01; 422/82.05; 204/403.11; 204/403.02; 204/407
(58) Field of Search ............................. 422/58, 61, 66, 422/68.1, 82.01, 82.05; 436/43–44, 150, 164, 166, 169, 808; 600/583–584; 204/403.02, 403.11, 407

(56) References Cited

U.S. PATENT DOCUMENTS

| | | |
|---|---|---|
| 2,641,358 A | 6/1953 | Santo |
| 3,393,831 A | 7/1968 | Stewart |
| 3,589,557 A | 6/1971 | Johnson |
| 4,114,780 A | 9/1978 | Sharon |
| 4,187,077 A | 2/1980 | Covington et al. |
| 4,190,420 A | 2/1980 | Covington et al. |
| RE30,895 E | 4/1982 | Butera |
| 4,474,892 A | * 10/1984 | Murad et al. ............... 436/513 |

(Continued)

FOREIGN PATENT DOCUMENTS

| | | |
|---|---|---|
| EP | 0 283 285 | 9/1988 |
| WO | WO 86/00513 | 1/1986 |
| WO | WO 94/10558 | 5/1994 |
| WO | WO 98/47007 | 10/1998 |
| WO | WO99/44508 | 9/1999 |
| WO | WO 01/23885 | 4/2001 |
| WO | WO 01/63272 | 8/2001 |
| WO | WO 01/64105 | 9/2001 |
| WO | WO 02/08753 | 1/2002 |

*Primary Examiner*—Lyle A. Alexander
(74) *Attorney, Agent, or Firm*—Susan C. Tall; Carol M. LaSalle; Boziceivic, Field & Francis, LLP

(57) ABSTRACT

Devices and methods for determining the concentration of an analyte in a physiological sample are provided. The subject devices are meters characterized by having an internal structure that includes a test strip selecting element having a continuously reduced cross-sectional area configured to select a single test strip at a time and means for determining the concentration of an analyte in a physiological sample applied to the selected test strip. In the subject methods for containing at least one test strip and dispensing a single test strip at a time, a meter having at least one test strip contained therein is provided. The meter is positioned with respect to the ground to cause the single test strip to move from a contained position to a dispensed position. The subject invention also includes kits for use in practicing the subject methods.

35 Claims, 13 Drawing Sheets

U.S. PATENT DOCUMENTS

| | | |
|---|---|---|
| 4,717,018 A | 1/1988 | Sacherer |
| 4,817,820 A | 4/1989 | Heiland |
| 4,911,344 A | 3/1990 | Kahler |
| 5,328,082 A | 7/1994 | Fritz et al. |
| 5,409,133 A | 4/1995 | Gringer |
| 5,489,414 A | 2/1996 | Schreiber et al. |
| 5,510,266 A | 4/1996 | Bonner et al. |
| 5,534,224 A | 7/1996 | Abe |
| 5,575,403 A | 11/1996 | Charlton et al. |
| 5,630,986 A | 5/1997 | Charlton et al. |
| 5,660,791 A | 8/1997 | Brenneman et al. |
| 5,736,103 A | 4/1998 | Pugh |
| 5,757,666 A | 5/1998 | Schreiber et al. |
| 5,759,010 A | 6/1998 | Jacobs et al. |
| 5,797,693 A | 8/1998 | Jaeger |
| 5,863,800 A | 1/1999 | Eikmeier et al. |
| 5,971,941 A | 10/1999 | Simons et al. |
| 5,989,917 A | 11/1999 | McAleer et al. |
| 6,036,924 A | 3/2000 | Simons et al. |
| 6,228,100 B1 | 5/2001 | Schraga |
| 6,295,506 B1 | 9/2001 | Heinonen et al. |

* cited by examiner

ANALYTE CONCENTRATION DETERMINATION METERS AND METHODS OF USING THE SAME

FIELD OF THE INVENTION

The field of this invention is analyte concentration meters.

BACKGROUND OF THE INVENTION

Analyte concentration determination in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like. In response to this growing importance of analyte concentration determination, a variety of analyte concentration determination protocols and devices for both clinical and home testing have been developed. Many such protocols employ test strips to perform the testing.

Before testing can begin, an individual seeking to determine the presence and/or concentration of an analyte in a physiological sample must first obtain a test strip, apply a sample thereto, and obtain the results, where the results are oftentimes obtained automatically with a meter and thus require the additional step of engaging an obtained test strip with a meter. However, this multi-step process is not without difficulty, especially for individuals who suffer from diminished hand-eye coordination and/or diminished finger sensation. For example, persons with diabetes typically have either or both impaired vision and diminished finger sensation or other dexterity problems. Such persons must use test strips to test their blood glucose levels a number of times a day.

To begin, a test strip must first be obtained. The ability to easily obtain a test strip, particularly a single test strip from amongst a plurality of test strips housed in a test strip container, may be difficult, for instance for those persons with diminished hand-eye coordination or finger sensation, as mentioned above. The typical test strip is only several millimeters in width and length and, thus, difficult to grasp and manipulate.

The most basic test strip containers are simple storage reservoirs where the test strips are retained inside and manually removed. However, it is often difficult to easily extract a test strip from these containers. These containers are usually shaped and sized to hold a plurality of test strips and to completely encompass the test strips inside so as to protect the test strips from light, humidity, and other environmental contaminants including oils and the like from an individual's hands, where such protection is necessary to insure the precision, accuracy and overall integrity of the test result.

An exemplary embodiment of such a simple test strip container is shown in FIG. 1. To obtain a single test strip from such a conventional test strip container to begin a test, an individual has two options for removing a test strip. In one option, an individual may simply turn the container upside down to pour a test strip out. This, as is apparent, has significant disadvantages as one or all of the test strips stored inside the container may quickly spill out and become contaminated or damaged. In a second option, an individual places a finger inside the container to try to grasp a single test strip from amongst a plurality of test strips without damaging or contaminating any of the strips in the process. However, such a method is difficult for individuals who have either or both impaired vision and diminished finger sensation and oftentimes results in an individual inadvertently contacting portions of the test strip that should not be touched, such as testing or reaction areas (i.e., areas on the strip having testing reagents, etc.) and the like, where such contact can impart contaminants and cause erroneous testing results. Similarly, other test strips may be inadvertently contacted resulting in erroneous testing results of those test strips as well.

More complex test strip containers have been developed to try to overcome some of the disadvantages associated with the simple test strip containers described above (see for example U.S. Pat. Nos. 5,575,403, 5,489,414; 5,630,986; 5,510,266). However, these, too, have certain disadvantages. For example, these devices often require a degree of physical dexterity and visual acuity that may be lacking in certain individuals who use the containers. Also, due to the complexity of the devices, i.e., the numbers of components forming the containers, the cost of manufacture increases and thus the cost to the user increases. Furthermore, typically such test strip containers require the test strips to be stacked in an orderly or precise manner therein. This too adds steps to the manufacturing process and thus increases costs.

In those instances where analyte concentration determination is performed automatically with a meter, once a test strip is finally obtained from a test strip container, the test strip must be associated with the meter, either before or after sample is applied thereto. Accordingly, grasping the test strip, an individual must engage the test strip with the meter so that the meter may "read" the test strip and determine the concentration of an analyte in the sample applied to the test strip. As is apparent, this increases complexity to the analyte concentration process and may be difficult for many individuals such as the above-described diabetic who might have diminished visual and/or finger sensation. Furthermore, while trying to manipulate the test strip into the appropriate position within the meter, an individual may inadvertently contact portions of the test strip that should not be touched thereby imparting contaminants thereto.

As such, there is continued interest in the development of new devices and methods for use in analyte concentration determination. Of particular interest would be the development of such devices and methods in which the test strip dispenser and meter are integrated into a single device, are easy and inexpensive to manufacture, have minimal components, are easy to use, particularly for visually and dextrally impaired individuals, are portable and which minimize damage and/or contamination to test strips.

SUMMARY OF THE INVENTION

Devices and methods for determining the concentration of an analyte in a physiological sample are provided. The subject devices are meters characterized by having an internal structure that includes a test strip selecting element having a continuously reduced cross-sectional area configured to select a single test strip at a time and means for determining the concentration of an analyte in a physiological sample applied to the selected test strip. In the subject methods for containing at least one test strip and dispensing a single test strip at a time, a meter having at least one test strip contained therein is provided. The meter is positioned with respect to the ground to cause the single test strip to move from a contained position to a dispensed position. The subject invention also includes kits for use in practicing the subject methods.

BRIEF DESCRIPTION OF THE DRAWINGS

FIG. 10A illustrates a cut-away view of a subject meter having a plurality of test strips held therein and the meter is held in a substantially upright position. FIG. 10B illustrates the meter of FIG. 10A positioned in a substantially upside down position where a single test strip is selected and dispensed. FIG. 10C illustrates the application of sample to the dispensed test strip of FIG. 10B.

FIG. 13A illustrates an exemplary embodiment of a test strip movement limiting element in a first position whereby it is positioned adjacent an exterior wall of a slot of a test strip selecting element and an exemplary embodiment of a test strip securing element in a first position whereby it protrudes partially into the interior of the slot. FIG. 13B illustrates the test strip movement limiting element of FIG. 13A in a second position whereby it protrudes perpendicularly into the interior of the slot such that it blocks a test strip from completely traveling out of the slot and out of the dispensing outlet. Test strip securing element of FIG. 13A is in a second position whereby it is deflected out of the interior of the slot by test strip movement limiting element. FIG. 13C illustrates the test strip movement limiting element of FIGS. 13A and 13B positioned back in a first position adjacent an exterior wall of the slot and test strip securing element back in a first position whereby it protrudes partially into the interior of the slot such that it secures the blocked, dispensed test strip in an appropriate position in the dispensing outlet of the meter so that the test strip is prevented from completely falling out of the dispensing outlet and sample may be applied thereto.

DETAILED DESCRIPTION OF THE INVENTION

Figure 1:
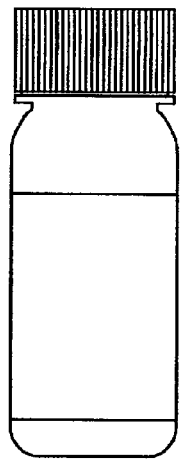
FIG. 1 shows an exemplary embodiment of a conventional test strip container.

Devices and methods for determining the concentration of an analyte in a physiological sample are provided. The subject devices are meters characterized by having an internal structure that includes a test strip selecting element having a continuously reduced cross-sectional area configured to select a single test strip at a time and means for determining the concentration of an analyte in a physiological sample applied to the selected test strip. In the subject methods for containing at least one test strip and dispensing a single test strip at a time, a meter having at least one test strip contained therein is provided. The meter is positioned with respect to the ground to cause the single test strip to move from a contained position to a dispensed position. The subject invention also includes kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a reagent" includes a plurality of such reagents and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject devices are described first. Next, a description of the subject methods is provided, followed by a review of kits which include the subject devices.

Devices

As summarized above, devices are provided for determining the concentration of an analyte in a physiological sample. Particularly, test strip meter devices are provided for easily selecting and dispensing a test strip therefrom for use, and commonly the subject meters provide for the easy dispensation of a single test strip from amongst a plurality of test strips, i.e., dispenses each test strip separately or one test strip at a time. The subject meters also automatically determine the concentration of an analyte in a physiological sample applied to the dispensed test strip, where the meters are configured to determine analyte concentration without removing or otherwise further manipulating a dispensed test strip.

The subject invention is suitable for dispensing any type of test strip, for example electrochemical and calorimetric or photometric (i.e., optical) type test strips as are known in the art, where such test strips find use in the determination of a wide variety of different analyte concentrations, where representative analytes include, but are not limited to, glucose, cholesterol, lactate, alcohol, and the like. In many embodiments, the test strips used with the subject invention are used to determine the glucose concentration in a physiological sample, e.g., interstitial fluid, blood, blood fractions, constituents thereof, and the like. In further describing the subject invention, a review of representative calorimetric and electrochemical test strips is provided first to provide a proper foundation for the subject invention, where such a review is by way of example and is not intended to limit the scope of the invention. In other words, it will be apparent that a wide variety of test strips, including, but not limited to, the representative colorimetric and electrochemical test strips described herein, may be suitable for use with the present invention. The review of suitable test strips is followed by a description of the subject test strip meter devices and the subject methods. Finally, a description of kits for use in practicing the subject methods is provided.

Representative Colorimetric Test Strips

Figure 2A:
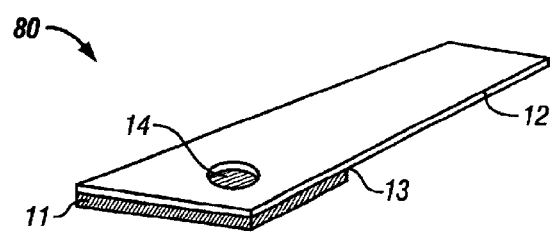
FIG. 2A shows an exemplary embodiment of a representative colorimetric test strip suitable for use with the subject invention.

The colorimetric or photometric (herein used interchangeably) reagent test strips employed in these embodiments of the subject invention are generally made up of at least the following components: a matrix 11 for receiving a sample, a reagent composition (not shown as a structural component) that typically includes one or more members of an analyte oxidation signal producing system and a support element 12. The calorimetric test strips are usually configured and adapted to be received in an automated meter, as described below, for automatically determining the concentration of an analyte. An exemplary embodiment of a representative colorimetric test strip is shown in FIG. 2A. FIG. 2A shows calorimetric test strip 80 in which a matrix 11 is positioned at one end of support element 12 with an adhesive 13. A hole 14 is present in the support element 12 in the area of matrix 11 in which a sample can be applied to one side of the matrix 11 and a reaction can be detected on an opposite side of matrix 11. The components of an exemplary calorimetric test strip will now be described in more detail.

Matrix

Matrix 11 that is employed in the subject test strips is an inert matrix which provides a support for the various members of the signal producing system, described below, as well as the light absorbing or chromogenic product produced by the signal producing system, i.e., the indicator. Matrix 11 is configured to provide a location for the physiological sample, e.g., blood, application and a location for the detection of the light-absorbing product produced by the indicator of the signal producing system. As such, matrix 11 is one that is permissive of aqueous fluid flow through it and provides sufficient void space for the chemical reactions of the signal producing system to take place. A number of different matrices have been developed for use in various analyte detection assays, which matrices may differ in terms of materials, dimensions and the like, where representative matrices include, but are not limited to, those described in U.S. Pat. Nos.: 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference. In principle, the nature of matrix 11 is not critical to the subject test strips and therefore is chosen with respect to other factors, including the nature of the instrument which is used to read the test strip, convenience and the like. As such, the dimensions and porosity of the test strip may vary greatly, where matrix 11 may or may not have pores and/or a porosity gradient, e.g. with larger pores near or at the sample application region and smaller pores at the detection region. Materials from which matrix 11 may be fabricated vary, and include polymers, e.g. polysulfone, polyamides, cellulose or absorbent paper, and the like, where the material may or may not be functionalized to provide for covalent or non-covalent attachment of the various members of the signal producing system.

Signal Producing System

In addition to matrix 11, the subject test strips further include one or more members of a signal producing system which produces a detectable product in response to the presence of analyte, which detectable product can be used to derive the amount of analyte present in the assayed sample. In the subject test strips, the one or more members of the signal producing system are associated, e.g., covalently or non-covalently attached to, at least a portion of (i.e., the detection region) the matrix, and in many embodiments to substantially all of the matrix.

In certain embodiments, e.g., where glucose is the analyte of interest, the signal producing system is an analyte oxidation signal producing system. By analyte oxidation signal producing system is meant that in generating the detectable signal from which the analyte concentration in the sample is derived, the analyte is oxidized by one or more suitable enzymes to produce an oxidized form of the analyte and a corresponding or proportional amount of hydrogen peroxide. The hydrogen peroxide is then employed, in turn, to generate the detectable product from one or more indicator compounds, where the amount of detectable product generated by the signal measuring system, i.e. the signal, is then related to the amount of analyte in the initial sample. As such, the analyte oxidation signal producing systems present in the subject test strips are also correctly characterized as hydrogen peroxide based signal producing systems.

As indicated above, the hydrogen peroxide based signal producing systems include an enzyme that oxidizes the analyte and produces a corresponding amount of hydrogen peroxide, whereby corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the first enzyme may be: glucose oxidase (where the analyte is glucose); cholesterol oxidase (where the analyte is cholesterol); alcohol oxidase (where the analyte is alcohol); lactate oxidase (where the analyte is lactate) and the like. Other oxidizing enzymes for use with these and other analytes of interest are known to those of skill in the art and may also be employed. In those preferred embodiments where the reagent test strip is designed for the detection of glucose concentration, the first enzyme is glucose oxidase. The glucose oxidase may be obtained from any convenient source, e.g. a naturally occurring source such as Aspergillus niger or Penicillum, or recombinantly produced.

A second enzyme of the signal producing system may be an enzyme that catalyzes the conversion of one or more indicator compounds into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g. Y. Ci, F. Wang; Analytica Chimica Acta, 233 (1990), 299–302.

The indicator compound or compounds, e.g., substrates, are ones that are either formed or decomposed by the hydrogen peroxide in the presence of the peroxidase to produce an indicator dye that absorbs light in a predetermined wavelength range. Preferably the indicator dye absorbs strongly at a wavelength different from that at which the sample or the testing reagent absorbs strongly. The oxidized form of the indicator may be a colored, faintly-colored, or colorless final product that evidences a change in color of the testing side of the membrane. That is to say, the testing reagent can indicate the presence of glucose in a sample by a colored area being bleached or, alternatively, by a colorless area developing color.

Indicator compounds that are useful in the present invention include both one-and two-component chromogenic substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, incorporated herein by reference), or 4-aminoantipyrine and the other component is an aromatic amine, aromatic alcohol, conjugated amine, conjugated alcohol or aromatic or aliphatic aldehyde. Exemplary two-component systems are 3methyl-2-benzothiazolinone hydrazone hydrochloride (MBTH) combined with 3-dimethylaminobenzoic acid (DMAB); MBTH combined with 3,5-dichloro-2hydroxybenzene-sulfonic acid (DCHBS); and 3-methyl-2-benzothiazolinonehydrazone N-sulfonyl benzenesulfonate monosodium (MBTHSB) combined with 8-anilino-1 naphthalene sulfonic acid ammonium (ANS). In certain embodiments, the dye couple MBTHSB-ANS is preferred.

In yet other embodiments, signal producing systems that produce a fluorescent detectable product (or detectable non-fluorescent substance, e.g. in a fluorescent background) may be employed, such as those described in: Kiyoshi Zaitsu, Yosuke Ohkura: New fluorogenic substrates for Horseradish Peroxidase: rapid and sensitive assay for hydrogen peroxide and the Peroxidase. Analytical Biochemistry (1980) 109, 109–113.

Support Element

Matrix 11 is usually attached to a support element 12. Support element 12 may be of a material that is sufficiently rigid to be inserted into an automated device such as a meter without undue bending or kinking. Matrix 11 may be attached to support element 12 by any convenient mechanisms, e.g., clamps, adhesive, etc., herein shown attached using an adhesive 13. In many embodiments, support member 12 is made of material such as polyolefins, e.g., polyethylene or polypropylene, polystyrene or polyesters. Consequently, the length of the support element 12 typically dictates or corresponds to the length of the test strip.

Regardless of whether or not the length of support element 12 dictates or corresponds to the length of test strip 80, the total length of the test strip 80 generally ranges from about 5 mm to about 80 mm, usually from about 15 mm to about 65 mm and more usually from about 40 mm to about 55 mm, the width of the test strip 80 typically ranges from about 2 mm to about 35 mm, usually from about 5 mm to about 20 mm and more usually from about 7 mm to about 15 mm and the thickness of the test strip 80 typically ranges from about 0.2 mm to about 7.5 mm, usually from about 0.4 mm to about 2.0 mm and more usually from about 0.6 mm to about 1.5 mm.

As described above, support element 12 is usually configured to enable test strip 80 to be used with or inserted into a meter. As such, support element 12, and thus test strip, is typically in the form of a substantially rectangular or square-like strip, where the dimensions of support element 12 vary according to a variety of factors, as will be apparent to those of skill in the art.

In using such a colorimetric test strip, sample is allowed to react with the members of the signal producing system to produce a detectable product that is present in an amount proportional to the initial amount present in the sample. The amount of sample that is introduced to matrix 11 of the test strip may vary, but generally ranges from about 0.1 to about 25.0 $\mu$l, usually from about 5.0 to 10.0 $\mu$l. The sample may be introduced to matrix 11 using any convenient protocol, where the sample may be injected, allowed to wick, or be otherwise introduced. The amount of detectable product, i.e., signal produced by the signal producing system, is then determined and related to the amount of analyte in the initial sample. In certain embodiments, automated meters that perform the above mentioned detection and relation steps are employed. The above described reaction, detection and relating steps, as well as instruments for performing the same, are further described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference.

Examples of such calorimetric reagent test strips suitable for use with the subject invention include, but are not limited to, those described in U.S. Pat. Nos. 5,049,487; 5,563,042; 5,753,452; 5,789,255, the disclosures of which are herein incorporated by reference.

Representative Electrochemical Test Strips

Figure 2B:
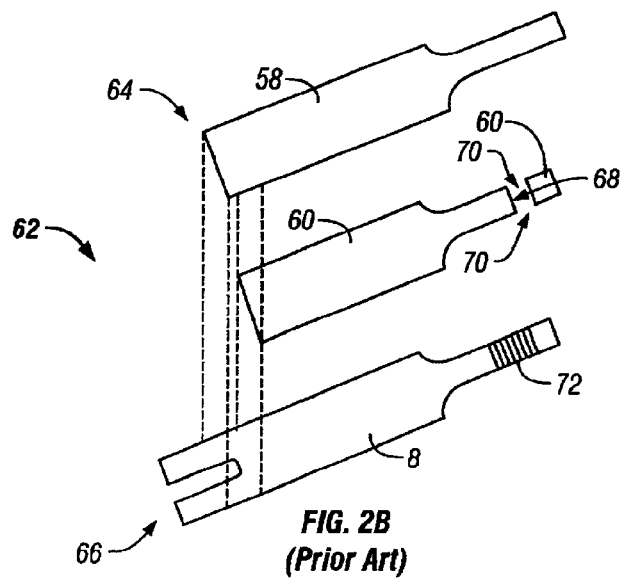
FIG. 2B shows an exploded view of an exemplary embodiment of a representative electrochemical test strip suitable for use with the subject invention.

Generally, the electrochemical test strips that find use with the subject invention are made up of two opposing metal electrodes separated by a thin spacer layer. In many embodiments a redox reagent system is located in the reaction area or zone. FIG. 2B shows an exploded view of an exemplary embodiment of a representative electrochemical test strip. Test strip 62 includes a reference electrode 64 and a working electrode 66 separated by a spacer layer 60 which is cut away to define a reaction area or zone 68 in communication with side ports 70 defined by a break in the spacer layer's coverage adjacent reagent system or composition 72.

The working electrode 66 and reference electrode 64 are further characterized in that at least the surfaces of the electrodes that face the reaction area 68 of the electrochemical cell in the strip is a metal, where metals of interest include palladium, gold, platinum, silver, iridium, carbon (conductive carbon ink), doped tin oxide, stainless steel and the like. In many embodiments, the metal is gold or palladium.

While in principle the entire electrode may be made of a metal, each of the electrodes is generally made up of an inert support material on the surface of which is present a thin layer of the metal component of the electrode. Any convenient inert support material may be employed in the subject electrodes, where typically the material is a rigid material that is capable of providing structural support to the electrode and, in turn, the electrochemical test strip as a whole. Suitable materials that may be employed as the inert support material include plastics, e.g., polyethylene terephthalate (PET), and glycol modified polyethylene terephthalate (PETG), polyimide, polycarbonate, polystyrene, silicon, ceramic, glass, and the like. In some instances, the support itself may be made of metal, especially one of those noted above. Generally, however, the electrode is a composite of a support coated with a metallic and/or conductive coating (such as palladium, gold, platinum, silver, iridium, carbon conductive carbon ink doped tin oxide or stainless steel When a metal-coated support is to be employed, its thickness will typically range from about 0.002 inch to about 0.014 inch (51 to 356 $\mu$m), usually from about 0.004 inch to about 0.007 inch (102 to 178 $\mu$m), while the thickness of the metal layer will typically range from about 10 nm to about 300 nm and usually from about 20 nm to about 40 nm.

As depicted, the working and reference electrodes 66 and 64, respectively, are generally configured in the form of elongate strips. Typically, the length of the electrodes ranges from about 0.25 inch to about 3 inches, usually from about 0.79 inch to about 1.5 inches. The width of the electrodes typically ranges from about 0.01 inch to about 0.30 inches, usually from about 0.1 inch to about 0.27 inches. In certain embodiments, the length of one of the electrodes is shorter than the other, wherein in certain embodiments it is about 0.135 inch (3.5 mm) shorter. Oftentimes, the electrode and spacer width is matched where the elements overlap. In certain embodiments, electrode 64 is about 1.365 inches (35 cm) long, electrode 66 is about 1.5 inches (3.8 cm) long, and each are about 0.25 inches (6.4 mm) wide at their maximum and about 0.103 inch (2.6 mm) wide at their minimum, reaction zone 68 and ports 70 are about 0.065 inches (1.65 mm) wide and the reaction zone 68 has an area of about 0.0064 in$^2$ (0.041 cm$^2$). The electrodes typically have a thickness ranging from about 10 nm to about 100 nm, usually ranging from about 18 nm to about 22 nm.

The reaction area or zone 68 in which activity occurs preferably has a volume of at least about 0.1 $\mu$l, usually at least about 0.3 $\mu$l and more usually at least about 0.6 $\mu$l, where the volume may be as large as 10 $\mu$l or larger. The size of zone 68 is largely determined by the characteristics of spacer layer 60. While spacer layer 60 is shown to define a rectangular reaction area in which the aforementioned activity occurs, other configurations are possible, (e.g., square, triangular, circular, irregular-shaped reaction areas, etc.). The thickness of spacer layer 60 generally ranges from about 0.001 inch to about 0.020 inch (about 25 to about 500 $\mu$m), usually from about 0.003 inch to about 0.005 inch (about 76 to about 127 $\mu$m), thus the total thickness of the test strip (electrodes and spacer layer) typically ranges from about 0.005 inch to about 0.050 inch, usually from about 0.010 inch to about 0.030 inch and more usually from about 0.015 inch to about 0.020 inch. The manner in which spacer layer 60 is cut also determines the characteristics of ports 70. The cross-sectional area of inlet and outlet ports 70 may vary as long as it is sufficiently large to provide an effective entrance or exit of fluid from reaction area 68.

As mentioned above, in many embodiments a reagent system or composition 72 is present in the reaction area, where reagent system 72 interacts with components in the fluid sample during the assay. Reagent systems of interest typically include a redox couple. The redox couple of the reagent composition, when present, is made up of one or more redox couple agents. A variety of different redox couple agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes, and the like. Other reagents that may be present in the reaction area include buffering agents, e.g., citraconate, citrate, malic, maleic, phosphate, "Good" buffers and the like. Yet other agents that may be present include: divalent cations such as calcium chloride, and magnesium chloride; surfactants such as Triton, Macol, Tetronic, Silwet, Zonyl, and Pluronic; stabilizing agents such as albumin, sucrose, trehalose, mannitol, and lactose. Examples of such a reagent test strips suitable for use with the subject invention include those described in U.S. Pat. No. 6,193,873 and copending and commonly owned U.S. application Ser. Nos. 09/497,304; 09/497,269; 09/736,788 and 09/746,116, the disclosures of which are herein incorporated by reference.

To use such an electrochemical test strip, an aqueous liquid sample (e.g., blood) is placed into the reaction zone. The amount of physiological sample that is introduced into the reaction area of the test strip may vary, but generally ranges from about 0.1 to 10 $\mu$l, usually from about 0.3 to 0.6 $\mu$l. The sample may be introduced into the reaction area using any convenient protocol, where the sample may be injected into the reaction area, allowed to wick into the reaction area, or be otherwise introduced through the ports. The component to be analyzed is allowed to react with the redox reagent coating to form an oxidizable (or reducible) substance in an amount corresponding to the concentration of the component to be analysed (i.e., analyte). The quantity of the oxidizable (or reducible) substance present is then estimated by an electrochemical measurement. The measurement that is made may vary depending on the particular nature of the assay and the device with which the electrochemical test strip is employed (e.g., depending on whether the assay is coulometric, amperometric or potentiometric). Measurement with strip 62 is preferably accomplished by way of an automated instrument or meter. Usually, measurement is taken over a given period of time following sample introduction into the reaction area. Methods for making electrochemical measurements are further described in U.S. Pat. Nos.: 4,224,125; 4,545,382; and 5,266,179; as well as WO 97/18465 and WO 99/49307 and WO 01/64105 publications, the disclosures of which are herein incorporated by reference.

Following detection of the electrochemical signal generated in the reaction zone, as described above, the amount of the analyte present in the sample introduced into the reaction zone is then typically determined by relating the electrochemical signal to the amount of analyte in the sample. In making this derivation, the measures electrochemical signal is usually compared to the signal generated from a series of previously obtained control or standard values, and determined from this comparison. In many embodiments, the electrochemical signal measurement steps and analyte concentration derivation steps, are performed automatically by a device designed to work with the test strip to produce a value of analyte concentration in a sample applied to the test strip, as noted above. A representative reading device for automatically practicing these steps, such that user need only apply sample to the reaction zone and then read the final analyte concentration result from the device, is further described in copending U.S. application Ser. No. 09/333,793 filed Jun. 15, 1999, the disclosure of which is herein incorporated by reference.

Analyte Concentration Determination Meters

As described above, the subject invention includes meter devices that easily select and dispense a single test strip at a time, such as the type of test strip described above, and automatically determine the concentration of an analyte in a physiological sample applied to the dispensed test strip. Typically, the subject devices select and dispense a single test strip from a plurality or aggregate of test strips. Usually the subject devices are configured to hold or accommodate from about 1 to about 100 test strips at one time, usually about 10 to about 75 test strips at one time and more usually from about 10 to about 25 test strips at one time, however the subject devices may be configured to hold a greater or fewer number of test strips at one time. In certain other embodiments, the subject devices are configured to be coupled, e.g., releasably coupled, to a test strip container which houses the test strips to be used with the subject device and where such coupling provides communication between a subject device and the test strip container such that test strip(s) retained in the test strip container are able to pass into the coupled subject device for subsequent selecting, dispensing and testing.

Figure 3A:
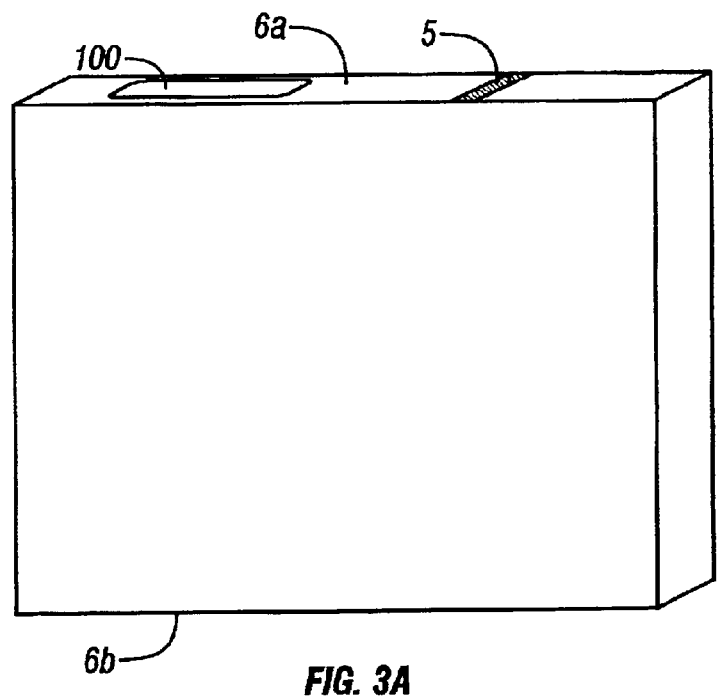
FIG. 3A shows an exterior view of an exemplary embodiment of a meter according to the present invention.
Figure 3B:
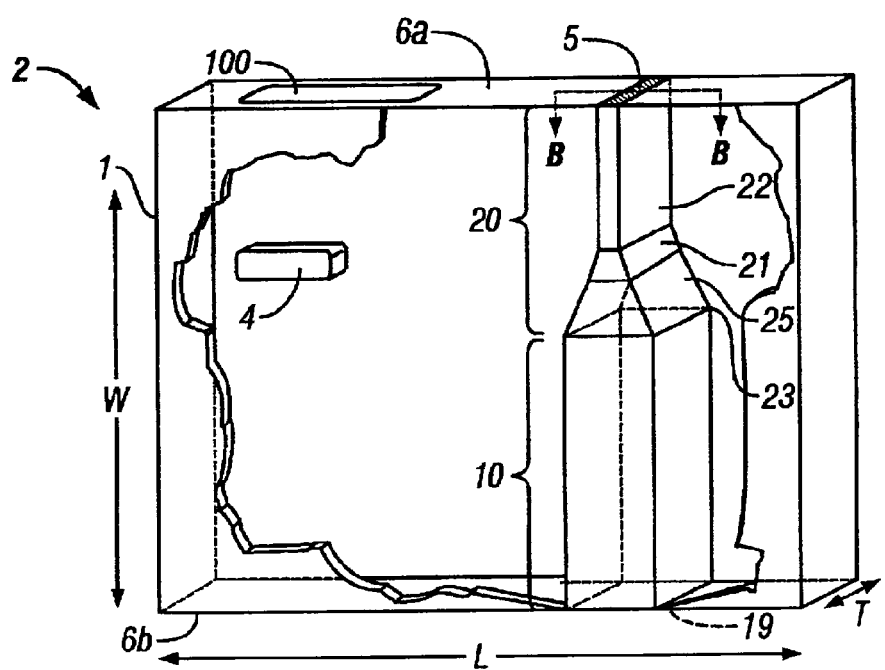
FIG. 3B shows a cut-away view of the meter of FIG. 3B showing the interior structure of the meter.

The subject test strip meter devices will now be described with reference to the Figures, where like numerals represent like components or features. FIG. 3A shows a view of the exterior an exemplary embodiment of the subject invention. Meter 2 includes dispensing outlet 5 and display means 100, as will be described in greater detail below. FIG. 3B shows a cut-away view of meter 2 of FIG. 3A and shows certain components associated with the interior structure thereof, as will be described below.

Generally, the subject meters are characterized by a housing 1 having an interior structure with a test strip selecting element 20. Housing 1 also includes dispensing outlet 5 positioned to be operably associated with a portion of the test strip selecting element 20 so that a test strip selected by the test strip selecting element 20 may be dispensed via dispensing outlet 5, as will be described in greater detail below. Furthermore, housing 1 also includes means for determining the concentration of an analyte in a physiological sample 4, i.e., any conventional optical or electrochemical analyte concentration determination means and display means 100 for communicating the results of an analyte concentration determination test to a user of the device e.g., one or more LED displays and/or one or more LCD displays and/or an audible message or signal.

The shape of housing 1 will necessarily vary depending on a variety of factors, where such factors include, but are not limited to, the type, size and number of test strips held or accommodated therein, and the like. Usually, housing 1 is shaped to be easily and comfortably held in a user's hand. FIGS. 3A and 3B shows housing 1 having a rectangular shape, but other shapes are possible as well. For example, housing 1 may be of a square, cylindrical, circular, disc, or elliptical shape, etc., or substantially so. Alternatively, the shape of housing 1 may be more complex such as a substantially irregular shape or the like.

Regardless of the shape, housing 1 has a top wall, top end or top side 6a and a bottom wall, bottom end or bottom side 6b. As shown in FIGS. 3A and 3B, dispensing outlet 5 is positioned through top wall 6a and thus top wall 6a may be characterized as the dispensing wall, end or side or of housing 1. In certain embodiments of the subject meters, a wall, e.g., bottom wall 6b or the like, may include optional resealable coupling means 19 for coupling or associating (usually releasably coupling) a separate test strip container device to housing 1 so as to provide communication therebetween so that test strips retained in the test strip container may move into the coupled housing so that a single test strip may be dispensed thereby. Optional coupling means may employ any convenient coupling mechanism such as snap fit, friction, threads and the like, as are known in the art.

The size of housing 1 may also vary depending on a variety of factors such as the type and size of test strips to be used therewith, and the number of test strips held or accommodated in housing 1, if applicable, and the like. Usually, housing 1 is sized to be easily and comfortably held in a user's hand and easily transportable. By way of example only and not limitation, in certain embodiments, the length L of housing 1 typically ranges from about 12 mm to about 200 mm, usually from about 40 mm to about 150 mm and more usually from about 65 to about 90 mm and the width W of housing 1 usually ranges from about 12 mm to about 100 mm, usually from about 20 mm to about 75 mm and more usually from about 25 mm to about 50 mm and the thickness T of housing 1 usually ranges from about 5 mm to about 50 mm, usually from about 15 mm to about 40 mm and more usually from about 20 to about 30 mm. Housing 1 may be manufactured from a variety of materials, where such materials will not substantially interfere with the analyte concentration determination, e.g., will not substantially interfere with the reagents of the test strips held therein. Representative materials that may be used in the manufacture of the subject housing include, but are not limited to, polymeric materials such as polytetrafluoroethylene, polypropylene, polyethylene, polystyrene, polycarbonate and blends thereof, metals such as stainless steel, aluminum and alloys thereof, Teflon™, siliceous material, e.g., glass materials, and the like.

Housing 1 is substantially moisture tight so as to maintain the integrity of test strips contained therein, where moisture may damage the test strips and cause erroneous testing results. As such, dispensing outlet 5 is capable of maintaining such a moisture tight interior environment using any suitable means. For example, dispensing outlet 5 may include a sealing element (not shown) such as a gasket, slideable member or other removable cover, etc., configured to provide a substantially moisture tight seal of or around dispensing outlet 5 when a test strip is not positioned therein. In certain embodiments, a test strip securing element, described below, provides a seal to dispensing outlet 5, in addition to or in place of another seal, e.g., a gasket or the like.

The subject housing may further include moisture absorbent reagents or components (not shown) such as desiccant material, silica gel and the like, where such material is capable of absorbing moisture from the environment surrounding the stored test strips. Such absorbent reagents or components may be retained in one or more compartments positioned inside housing 1.

As mentioned above, the subject devices are capable of selecting and dispensing a single test strip at a time for use. Accordingly, a feature of the subject devices is the presence of a test strip selecting element 20, shown in FIG. 3B, that is capable of selecting and dispensing a single test strip from within housing 1 so that the single test strip may be used. That is, where housing 1 holds a plurality of test strips, test strip selecting element 20 is capable of easily selecting a single test strip, e.g., it provides for the separation of a single test strip from other test strips, and positions it for use.

A feature of the test strip selecting element 20 is that it operates by simple manipulation or handling of meter 2 i.e., it does not require an individual to actuate the device or any component thereof, and thus is passively activated and particularly well suited for an individual who has dexterity problems such as diminished fingertip sensation and/or who is visually impaired. Accordingly, test strip selecting element 20 selects and dispenses a test strip for use when meter 2 is positioned in a particular orientation relative to the ground. More specifically, the test strip selecting element 20 selects and positions a test strip for use by a simple rotation or turning of meter 2 to a substantially upside down position.

Figure 6:
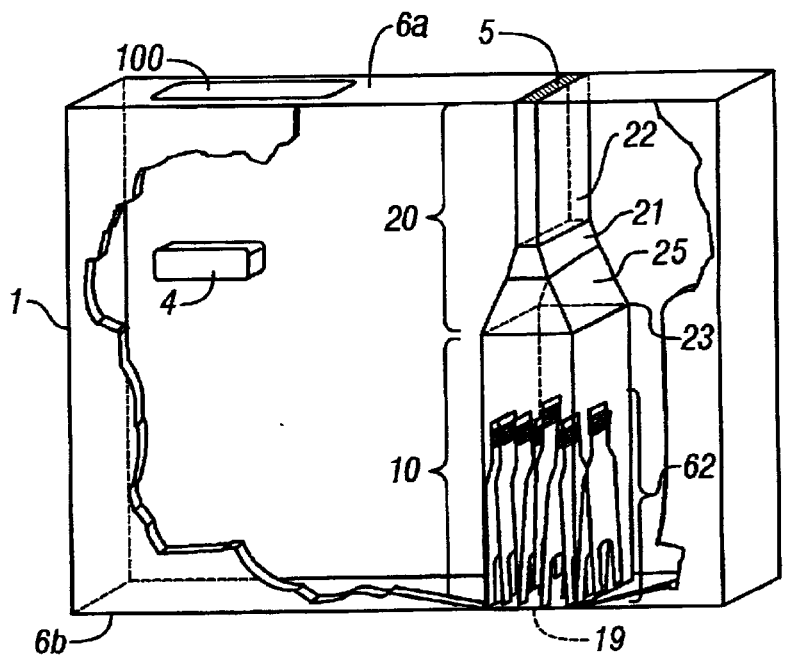
FIG. 6 shows the meter of FIG. 3B in a substantially upright position.
Figure 7:
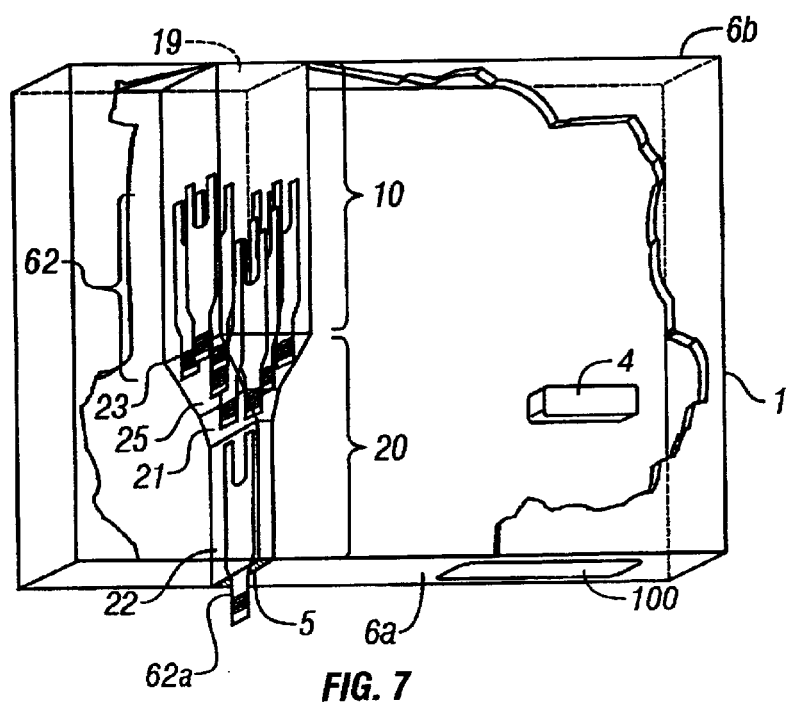
FIG. 7 shows the meter of FIG. 3B in a substantially upside down position.

FIG. 6 shows meter 2 of FIG. 3B having a plurality of test strips 62 contained in test strip area 10, i.e., test strips 62 are in a contained position within meter 2. As is apparent, the contained test strips need not be stacked in an orderly fashion. As noted above, test strip selecting element 20 is configured within housing 1 such that when housing 1 is appropriately positioned relative to the ground, test strips 62 move into test strip selecting element 20. By appropriate position is meant that meter 2 is positioned substantially upside down as shown in FIG. 7. That is, if meter 2 is originally oriented in a substantially upright orientation, then the device is turned or rotated so that the device is substantially upside down. By substantially upright is meant meter 2 is at an angle β (see FIGS. 9A and 9B) that ranges from about −30 to about +30 relative to the central axis C of meter 2 when the central axis C of meter 2 is perpendicular to the ground G and wall 6b is positioned closer to ground G than wall 6a is positioned with respect to the ground G. By substantially upside down is meant meter 2 is at an angle γ (see FIG. 9C) that ranges from about −20 to about +20 relative to the central axis C of meter 2 when the central axis C of meter 2 is positioned perpendicular to the ground G and wall 6a is positioned closer to the ground G than wall 6b is positioned with respect to the ground G.

The test strip selecting element 20 includes an area or cavity 25 having a continuously reduced diameter or continuously reduced cross-sectional area, as shown in FIG. 3B. As such, test strip selecting area may be as having a cavity that is substantially frustum-shaped. More specifically, cavity 25 has a substantially funnel-like shape such that it has walls that taper inwardly towards slot 22 of first end 21, e.g., substantially frustum-shaped cavity 25 may be characterized as having an internal diameter that decreases from second end 23 to first end 21. As shown in FIGS. 3 through 7, the diameter or cross-sectional area of substantially frustum-shaped cavity 25 gradually decreases from second side 23 to slot 22 of first side 21. Specifically, the diameter of substantially frustum-shaped cavity 25 of test strip selecting element 20 decreases to an ultimate diameter or area that only accommodates or is only permissive of a single test strip at a time.

The cross-sectional shape of substantially frustum-shaped cavity 25 may vary depending on a variety of factors such as the size and shape of the test strip to be dispensed, etc., The only limitation as to the shape of cavity 25 is that it is capable of funneling at least one test strip therethrough. Accordingly, the cross-sectional shape of substantially frustum-shaped cavity 25 may be rectangular, square, circular, or elliptical, etc. As such, the cross-sectional shapes of the exemplary embodiments of cavity 25 shown herein are for exemplary purposes only and are not intended to limit the scope of the invention.

Figure 4:
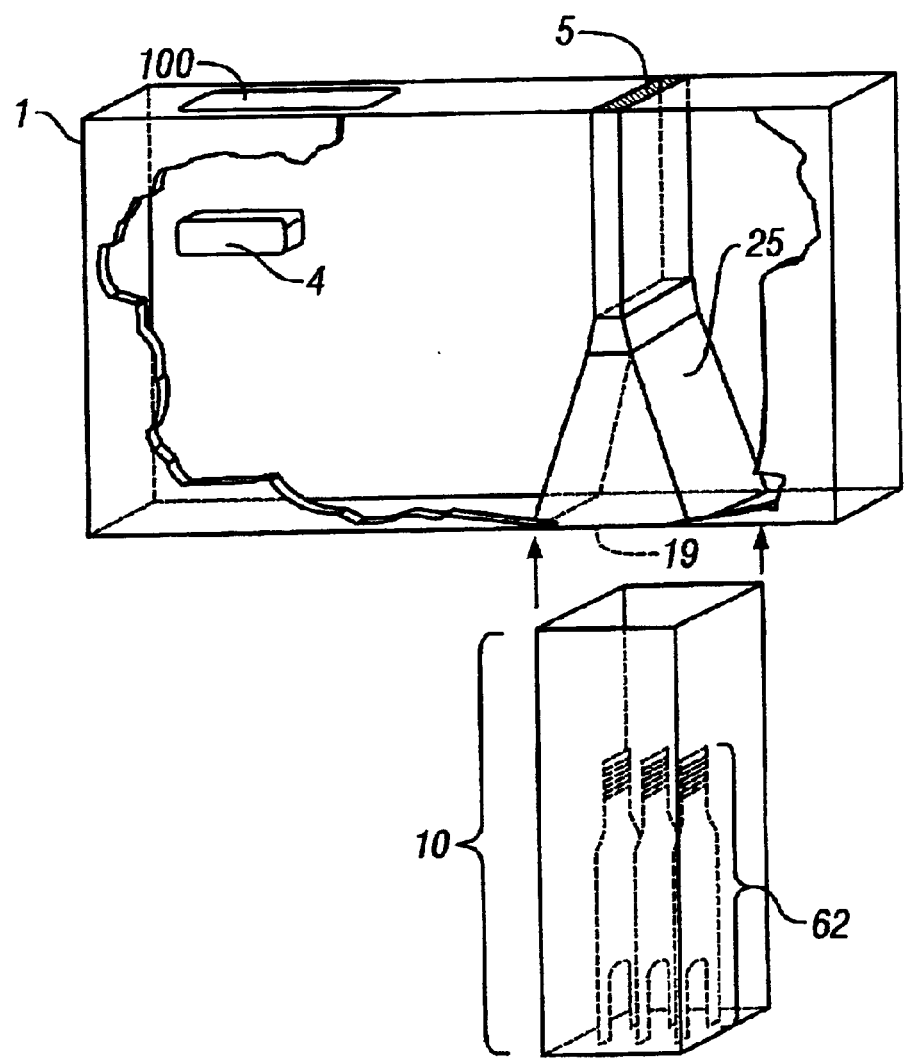
FIG. 4 shows a cut-away view of an exemplary embodiment of a meter according to the present invention having a separate test strip area capable of coupling to the meter.
Figure 5A:
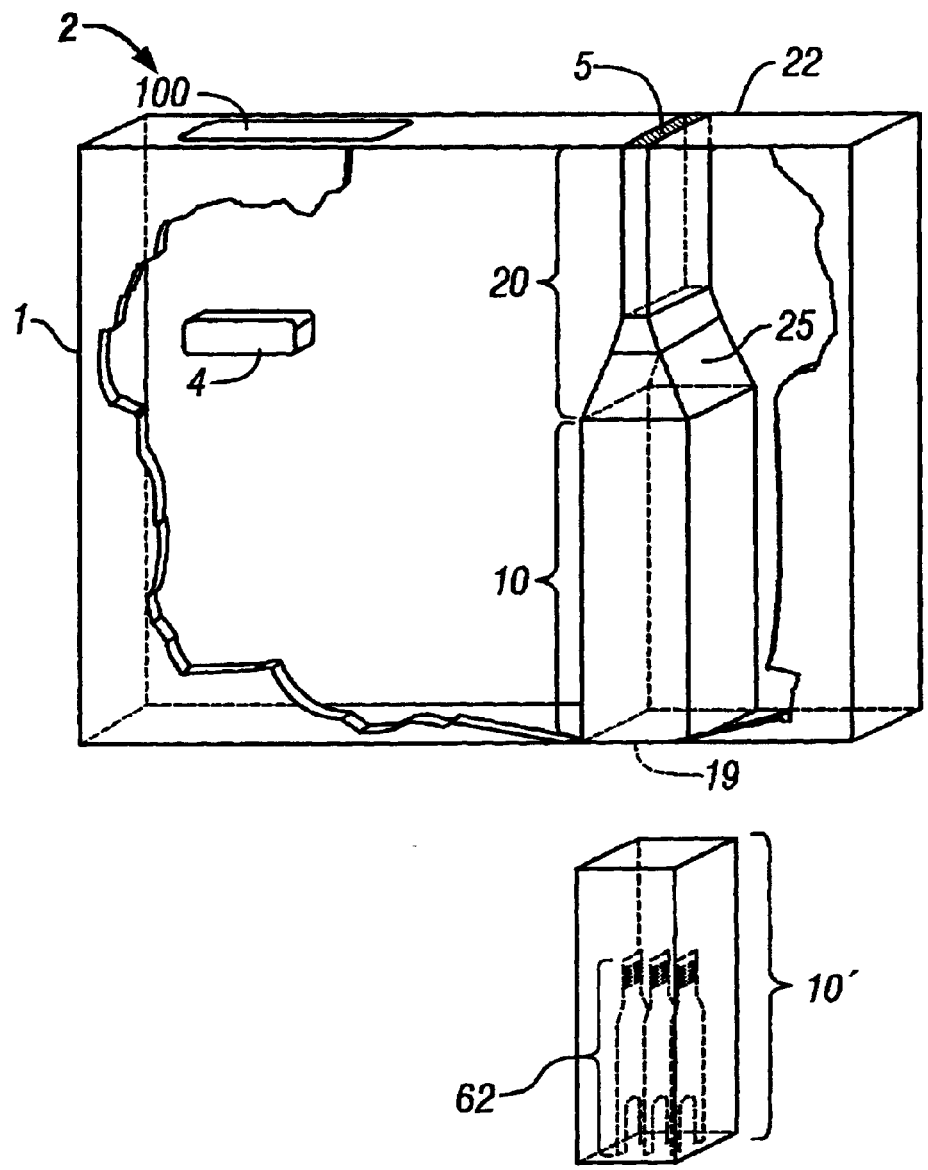
FIG. 5A shows a cut-away view of an exemplary embodiment of a meter according to the present invention having a separate test strip containing area in the interior thereof and a separate test strip area such as a separate test strip container.
Figure 5B:
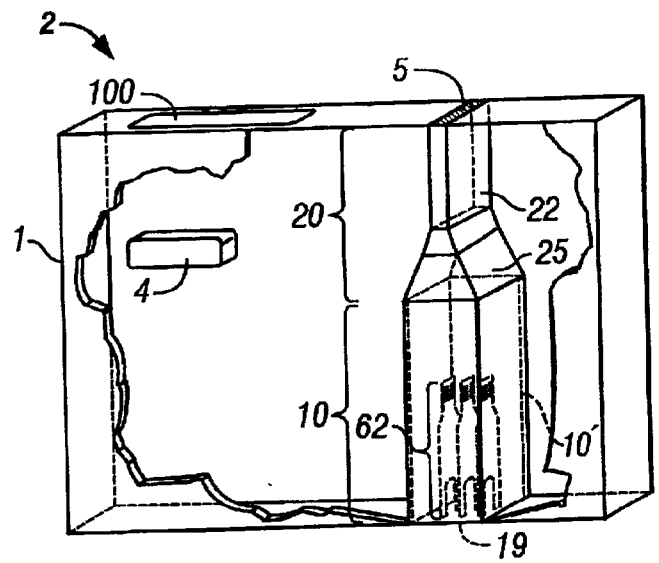
FIG. 5B shows the meter of FIG. 5A having the separate test strip area positioned in the interior of the meter.
Figure 5C:
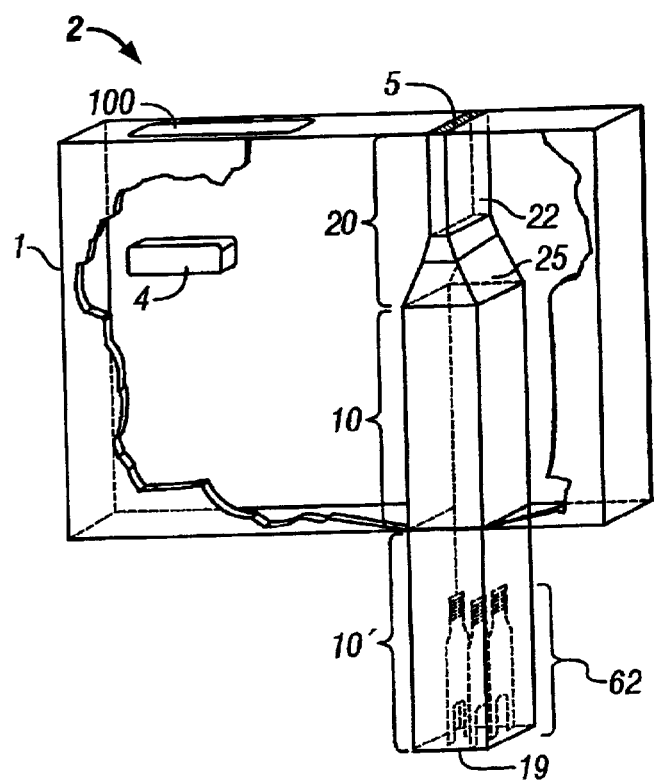
FIG. 5C shows the meter of FIG. 5A having the separate test strip area externally coupled to the meter.

Substantially frustum-shaped cavity 25 opens on second end 23, which is in direct communication with test strip area 10 for holding and/or containing one or more test strips, and more usually a plurality of test strips. Test strip area 10 may be positioned inside housing 1, i.e., an integral feature of housing 1 as shown in FIG. 3B, or may be a component that is coupled to and/or inserted into housing 1, such as a separate test strip container as shown in FIG. 4 containing a plurality of test strips 62 or may be a combination of the above, as shown in FIGS. 5A–5C. FIG. 5A shows meter 2 having test strip area 10, such as a test strip holding or receiving area or container, in the interior of housing 1, where test strip area 10 is configured to be associated with another, separate test strip area 10' that contains a plurality of test strips 62. FIG. 5B shows separate test strip area 10', such as a test strip container or dispenser, inserted into and received within test strip area 10 of meter 2. FIG. 5C shows another embodiment where separate test strip area 10', such as a test strip container or dispenser, is coupled to the exterior of housing 1 such that a passageway between separate test strip area 10' and test strip area 10 is provided therebetween.

The test strip selecting element 20 is configured such that one or more test strips that are caused to move from test strip area 10 through substantially frustum-shaped cavity 25, i.e., moved through second end 23 to first end 21, results in a single test strip selected at first end 21 of substantially frustum-shaped cavity 25. In other words, test strip selecting element 20 funnels at least one test strip through an area having a continuously decreasing cross-sectional area, i.e., a substantially frustum-shaped cavity 25, so as to ultimately select a single test strip in an opening or-slot 22 positioned at first end 21 of substantially frustum-shaped cavity 25. The remaining test strips are prevented from passing all the way through substantially frustum-shaped cavity 25 to slot 22 due to the configuration (size and/or shape) of cavity 25 and slot 22 and, as such, remain in cavity 25 of test strip selecting element 20 until selected for later use by an individual.

As described above, slot 22 is in communication with first end 21 of substantially frustum-shaped cavity 25. Accordingly, slot 22 is configured so that a single test strip moved through substantially frustum-shaped cavity 25 is selected in slot 22, which is sized and/or shaped for selecting or being permissive of only a single test strip therein at one time. As shown in FIG. 7 cavity 25 enables test strip selecting element 20 to select a single test strip 62a in slot 22 because the number of the test strips that are able to be accommodated in substantially frustum-shaped cavity 25 decreases from second side 23 to first side 21, where ultimately only one single test strip 62a is able to be accommodated in slot 22 and thus selected test strip 62a is separated from the rest of the test strips.

The size and/or shape of slot 22 need not necessarily correspond to that of a test strip, i.e., the size and/or shape of slot 22 may differ from the size and/or shape (width) of a test strip, as long as slot 22 enables a single test strip to be selected thereby, e.g., a test strip may be rectangular in shape and slot 22 may be of a shape other than rectangular. By way of example only and not limitation, in certain embodiments when housing 1 is used with test strips having lengths ranging from about 7 mm to about 76 mm, widths ranging from about 1.3 mm to about 8.0 mm and thicknesses ranging from about 127 $\mu$m to about 1270 $\mu$m, the length of the slot 22 will typically range from about 3 mm to about 50 mm, usually from about 5 mm to about 25 mm and more usually from about 6 mm to about 10 mm, the width slot 22 will typically range from about 0.026 cm to about 1.0 cm and more usually from about 0.250 cm to about 0.75 cm and the thickness or depth of slot 22 will typically range from about 0.3 cm to about 0.8 cm. Slot 22 may include openings to accommodate means for limiting test strip movement and means for securing a test strip, as will be described in more detail below.

Figure 8:
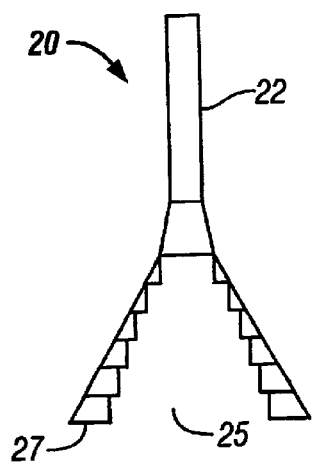
FIG. 8 shows an exemplary embodiment of a test strip selecting element according to the present invention having a directing element positioned in the interior.

In certain embodiments of the subject invention, such as illustrated in FIG. 8, the interior of the test strip selecting element 20 further includes a test strip directing element 27, i.e., the interior of the funnel-like cavity 25 includes a structure for directing at least one test strip therethrough. For example, a series of bumps or protrusions, studs, ribs steps, ridges, ledges or the like may be positioned on the interior of the test strip selecting element 20 to direct the test strip(s) towards the slot 22 and assist in separating a single test strip from others. The directing element 27 may be positioned in any suitable manner. For example, a series of ridges or steps may encircle the entire interior of the test strip selecting element 20 or may be positioned on a portion of the interior such as on two opposing sides of the test strip selecting element 20. Opposing steps may be offset or graduated in such a manner that the top of one step corresponds with the rise of an opposing step. FIG. 8 shows a cross sectional view through an exemplary test strip selecting element, such as a cross section taken along line B—B of test strip selecting element 20 of FIG. 3B. FIG. 8 shows test strip selecting element 20 having a series of steps or ridges 27 positioned at least on two opposing sides of the interior of the test strip selecting element 20.

As described above, the subject devices select and dispense a single test strip 62a for use, as shown in FIG. 7. As such, meter 2 includes a dispensing outlet 5 (shown in FIGS. 3A and 3B, for example), configured such that a test strip selected for use by test strip selecting element 20 is ultimately positioned in dispensing outlet 5 so that it is accessible by a user. Accordingly, dispensing outlet 5 is typically also dimensioned and/or sized to accommodate or be permissive of only a single test strip at a time. Usually, the dispensed test strip 62a is positioned in dispensing outlet 5 such that the sample receiving portion extends from the dispensing outlet 5 positioned in dispensing wall 6a, so that a user may readily apply sample to dispensed test strip 62a and determine the concentration of analyte in the sample. By "readily apply" is meant that the user may apply sample and determine analyte concentration without removing dispensed test strip 62a from meter 2 or otherwise further substantially manipulating test strip 62a. Test strip 62a may be secured in outlet 5 using appropriate means, as will be described in greater detail below.

Test strip selecting element 20 may be a unitary piece of construction with respect to housing 1, i.e., may be molded in housing 1, or may be a separate component that is attached to the interior structure of housing 1 by any convenient means, including welding, adhesives, friction, snap fit, etc., and any combination thereof. Typically, test strip selecting element 20 is constructed as a unitary piece with respect to housing 1.

Figure 11:
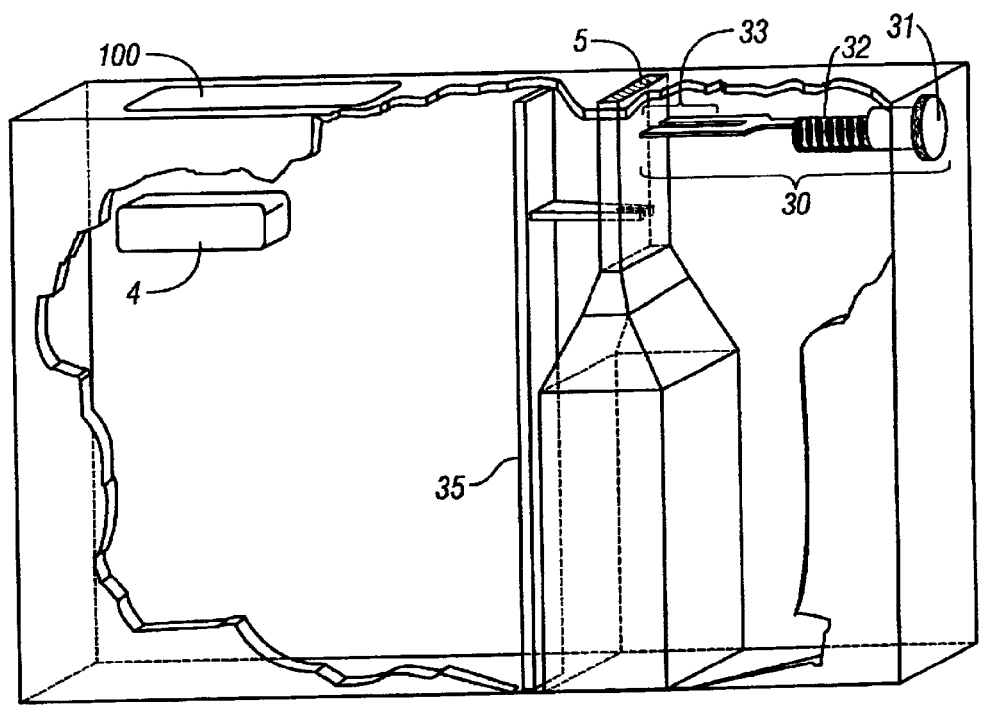
FIG. 11 shows a cut-away view of an exemplary embodiment of a subject meter having means for positioning and securing a test strip in an appropriate position in the dispensing outlet of the meter.

Housing 1 may also include a test strip movement limiting element and a test strip securing element configured to maintain and hold a dispensed test strip in an appropriate position in dispensing outlet 5 for sample application thereto. Test strip movement limiting element 30 (shown in FIG. 11) is configured to appropriately limit the movement of a test strip that is selected to be dispensed from dispensing outlet 5 of housing 1 such that only a portion of a selected test strip is able to move beyond test strip movement limiting element 30 so that only a portion of the test strip is able to protrude from outlet 5 and the remaining portion of the test strip is prevented from moving beyond test strip movement limiting element 30 and, as such, remains inside housing 1, i.e., inside slot 22.

As mentioned above, test strip movement limiting element 30 works with test strip securing element 35 (shown in FIG. 11) to maintain and secure a selected test strip in an appropriate position in outlet 5 so that sample may be applied to the test strip while the test strip remains associated with the meter. Test strip movement limiting element 30 and test strip securing element 35 may be positioned in any convenient location in the interior of meter 1, so long as they are positioned so that they are able to position and secure a test strip for dispensing, and more specifically in outlet 5 for dispensing.

Figure 12A:
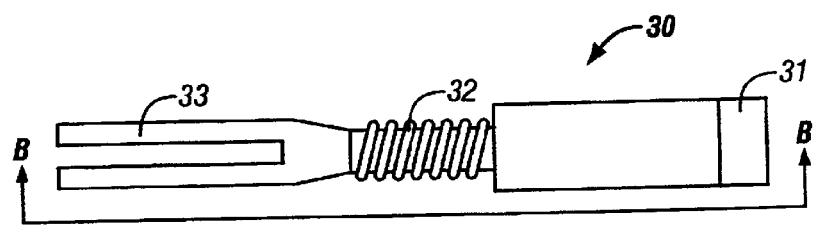
FIG. 12A shows a top view of an exemplary embodiment of a test strip movement limiting element according to the subject invention.
Figure 12B:
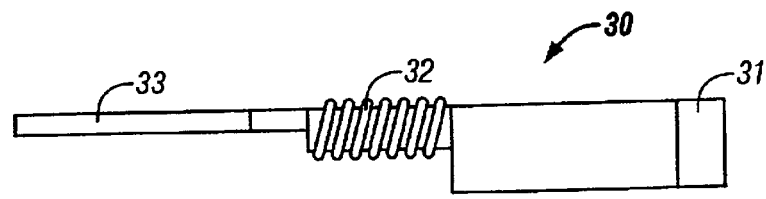
FIG. 12B shows a side view of the test strip movement limiting element of FIG. 12A.

An enlarged view of test strip movement limiting element 30 is shown in FIGS. 12A and 12B, which show a top view and side view taken along line B—B of FIG. 12A, respectively, of test strip movement limiting element 30. Test strip movement limiting element 30 includes trigger mechanism 31 accessible by a user of the meter, spring loaded actuator 32 and test strip block 33. As shown, test strip block 33 is pronged and thus is configured to position a test strip between the prongs thereof so as to block or limit the movement of a portion of a test strip from traveling beyond block 33. As such, in those embodiments employing such a test strip movement limiting element, slot 22 of test strip selecting element 20 will have appropriately configured openings to allow entrance of the prongs of test strip block 33 therethrough, perpendicularly to the longitudinal axis of slot 22. In this manner, the prongs of block 33 may engage a test strip that has been selected in slot 22, thereby blocking a portion of the test strip from moving beyond block 33 while allowing the remaining portion of the test strip to travel beyond block 33, the portion that is dimensioned to travel through the prongs of block 33, as will be described in greater detail below with reference to FIGS. 13A–13C.

Housing 1 of meter 2 also includes means for determining the concentration of an analyte in a physiological sample 4, where exemplary means electrochemical analyte concentration determination, where such means are well known in the art. That is, the present invention permits analyte concentration determination for both photometric or optical and electrochemical systems.

As described above, analyte concentration determination is generally based on one of two technologies. The first technology is the photometric or optical type, which is based on test strips that include a composition that changes color after blood if applied to the test strip. The color change is related to or is a measure of the concentration of an analyte. Means for analyte concentration determination in such systems generally include at least one light source, a detector for detecting absorbed or reflected light and processing means such as a microprocessor and the like. Representative means for determining the concentration of an analyte using a photometric or optical system adaptable for use with the subject invention include, but are not limited to, those described above, as well as those described in U.S. Pat. Nos. 5,304,468; 5,515,170; 5,843,692; 5,986,754; 6,084,660 and 6,268,162, the disclosures of which are herein incorporated by reference, where such adaption requires no more than routine experimentation.

The second technology is based on electrochemical principles and operates on the principle that blood applied to an electrochemical cell can cause an electrical signal-voltage, current or charge, depending on the type of meter, which can be related to the concentration of an analyte. Means for analyte concentration determination in such systems generally include at least means for applying an electric potential across the electrodes of the test strip, means for measuring electrical signals and processing means such as a microprocessor and the like. Representative means for determining the concentration of an analyte using an electrochemical system adaptable for use with the subject invention include, but are not limited to, those described above, as well as those described in U.S. Pat. Nos. 5,266,179; 5,366,609; 5,942, 102; 6,193,873 and WO/01/64105, the disclosures of which are herein incorporated by reference, where such adaption requires no more than routine experimentation.

The subject invention usually also incorporates means for presenting results of measurements acquired during the operation of the meter (not shown), i.e., display means, such as digital displays, e.g., one or more light-emitting diode (LED) displays, one more liquid crystal (LCD) displays and/or audio means, etc.

Methods

Also provided by the subject invention are methods for selecting and dispensing a single test strip and determining the concentration of an analyte in a physiological sample applied to the test strip. More specifically, methods are provided that enable a single test strip to be easily selected and dispensed so that it may be used for analyte concentration determination, for example by a visually and/or dextrally impaired individual such as a diabetic or the like. According to the subject methods, a subject meter, as described above, is provided. At least one test strip is caused to be held or accommodated in the interior thereof and the meter is handled or positioned in a manner to cause a single test strip to be selected, usually from amongst a plurality of test strips, and dispensed for use. Once a test strip is dispensed, physiological sample may be applied thereto and the concentration of an analyte in the sample may be determined. The subject methods provide a way in which an analyte concentration may be determined without the user removing or otherwise manipulating the test strip once it is dispensed. As is apparent, such methods minimize steps involved in test strip dispensing and also eliminate direct contact with test strips, thereby avoiding contamination of the test strips. In further describing the subject invention, selecting and dispensing a single test strip from a plurality of test strips will be used for exemplary purposes only and is in no way intend to limit the scope of the invention. As will be apparent, the subject methods include those instances where only a single test strip is provided for selection and dispensation, such that at least one test strip is provided in the subject methods.

As such, the first step is to provide a subject test strip meter device, as described above. At least one test strip is held in a test strip area of the meter or the meter is coupled to a device that has at least one test strip therein. More specifically, a subject meter may have test strips retained in the interior thereof, either preloaded, e.g., at the manufacturing site, or loaded by a user. Alternatively, a separate test strip containing device having at least one test strip therein may be coupled to the subject meter such that communication between the separate test strip container and the meter is provided, i.e., the test strip(s) retained inside the test strip container have access to the interior of the meter, as described above. Any convenient test strip containing device may be modified for use with the subject meters (see for example U.S. Pat. Nos. 4,835,234; 4,934,556; and 5,989, 917), where the modifications needed to adapt a test strip container for coupling with a subject meter require no more than routine experimentation. The one or more test strips are usually positioned in the test strip area of the meter such that the sample application portion of the test strip is the portion that protrudes from meter 2 when the test strip is dispensed.

Figure 9A:
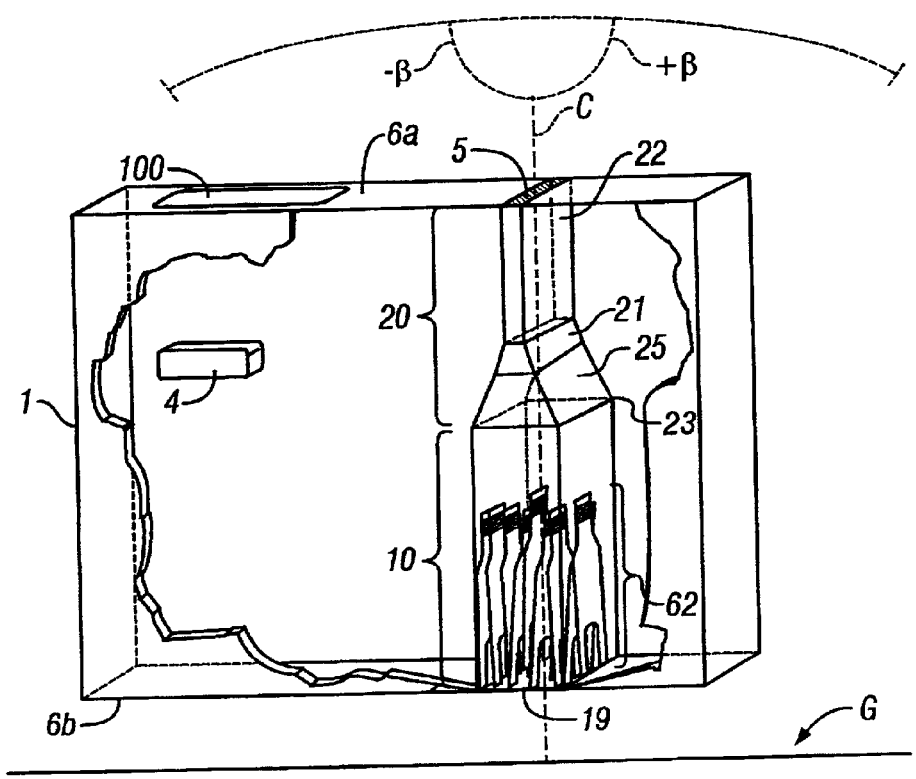
FIGS. 9A and 9B show the meter of FIG. 3B in a substantially upright position.
Figure 9B:
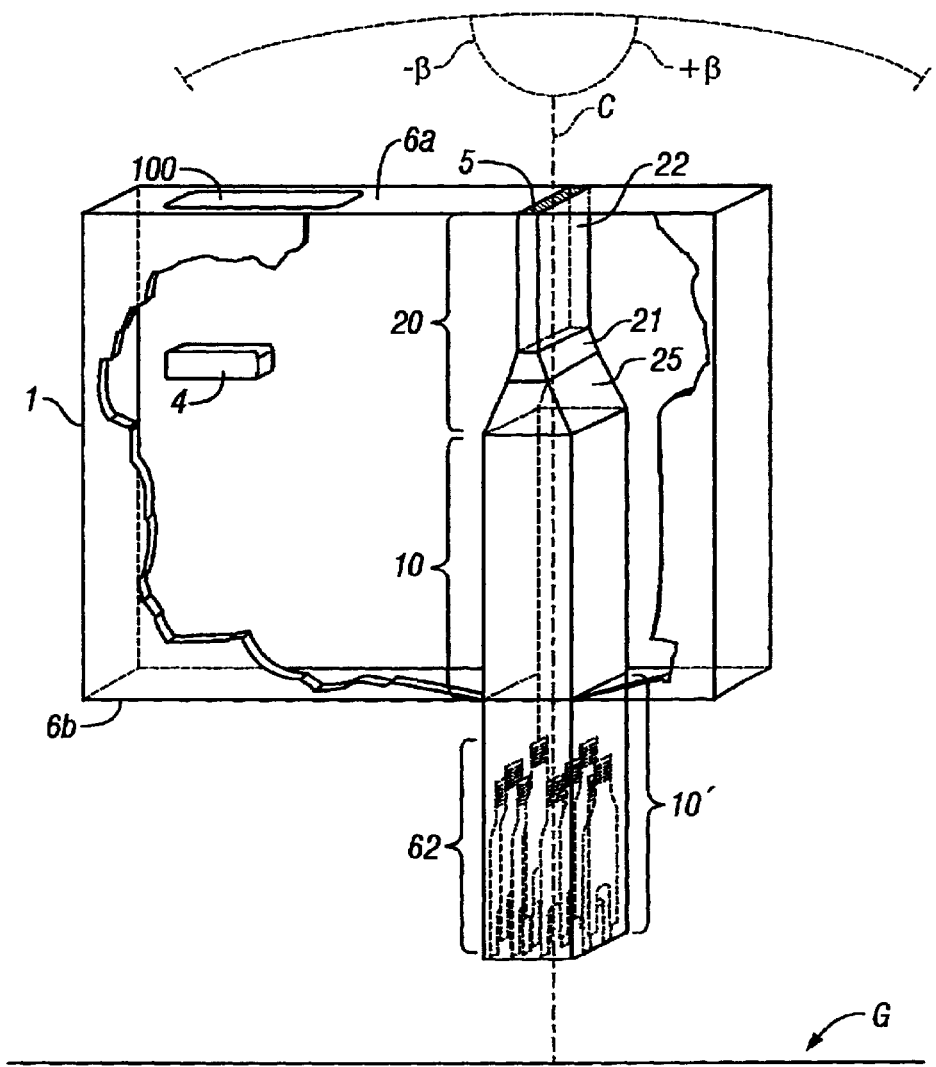
Figure 9C:
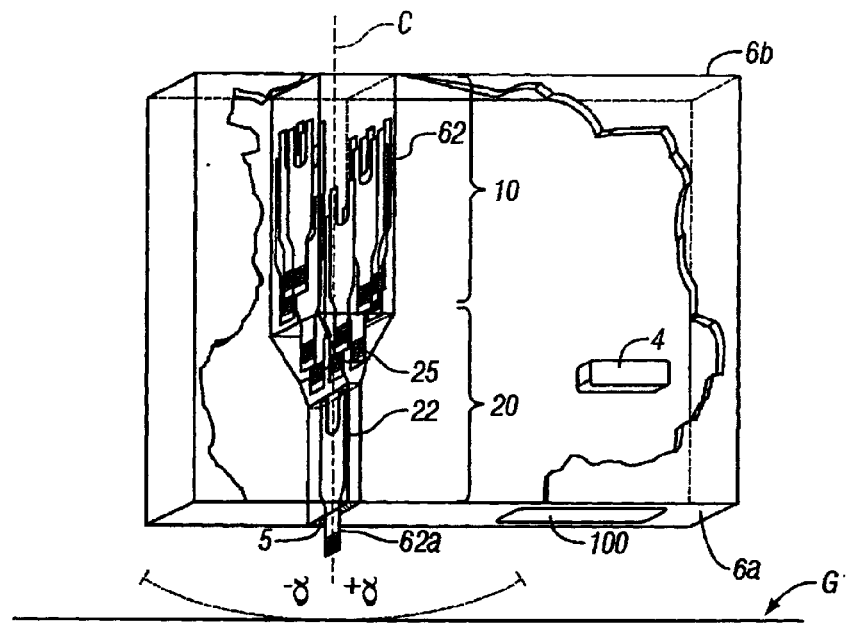
FIG. 9C shows the meter of FIG. 3B in a substantially upside down position.

Once the provision of a subject meter is met, and at least one test strip is associated with the interior thereof, the meter is positioned in a manner to cause the one or more test strips held, retained or associated with the interior of the meter to move towards the dispensing end of the meter, i.e., towards the side or wall of the meter that has a dispensing outlet. That is, the meter is positioned so that it is substantially upside down. FIGS. 9A and 9B show meter 2 in a substantially upright position having a plurality of test strips retained in a test strip area 10 of the interior of meter 2 and a plurality of test strips retained in a test strip area 10' of a separate container that is coupled to meter 2, respectively. FIG. 9C shows meter 2 in a substantially upside down position. By substantially upright is meant meter 2 is at an angle $\beta$ that ranges from about −30 to about +30 relative to the central axis C of meter 2 when the central axis C of meter 2 is positioned perpendicular to the ground G and wall 6b is closer to ground G than wall 6a is positioned with respect to the ground G. By substantially upside down is meant meter 2 is at an angle $\gamma$ that ranges from about −20 to about +20 relative to the central axis C of meter 2 when the central axis C of meter 2 is positioned perpendicular to the ground G and wall 6a is closer to the ground G than wall 6b is positioned relative to the ground G. In further describing the subject methods, meter 2 having a plurality of test strips 62 retained therein, as shown in FIG. 9A, will be used for exemplary purposes and is in no way intended to limit the scope of the invention. That is, the subject methods include all embodiments of the subject invention, unless noted otherwise.

Figure 10A:
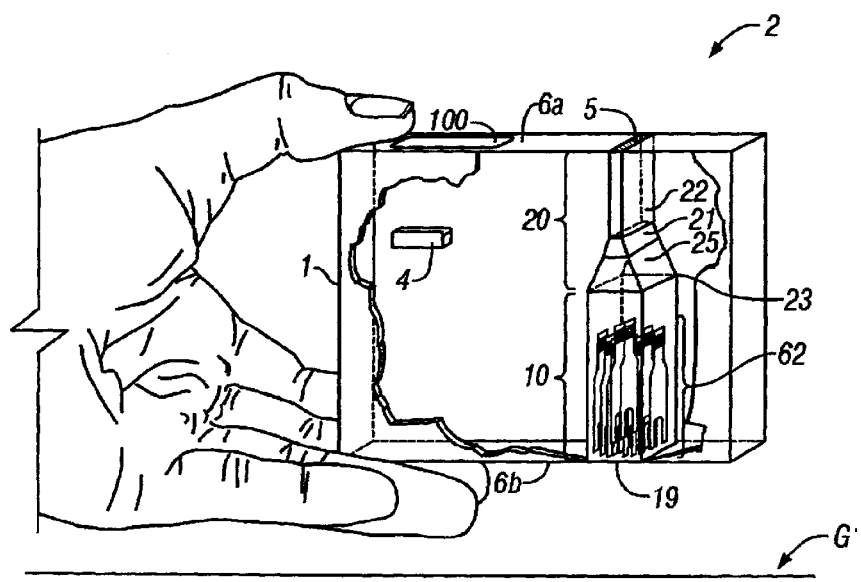
FIGS. 10A–10C illustrate the steps of the subject methods.
Figure 10B:
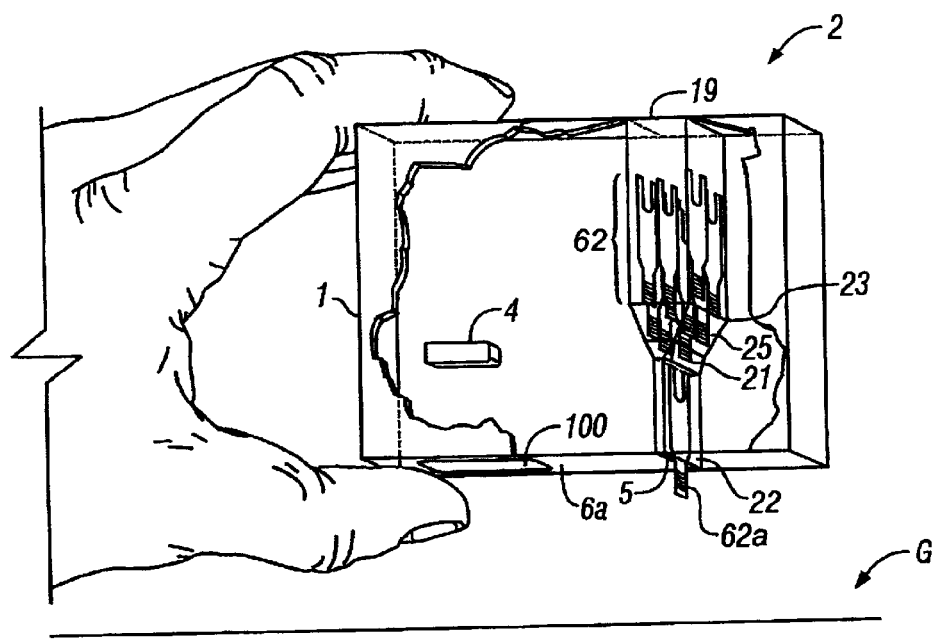
Figure 10C:
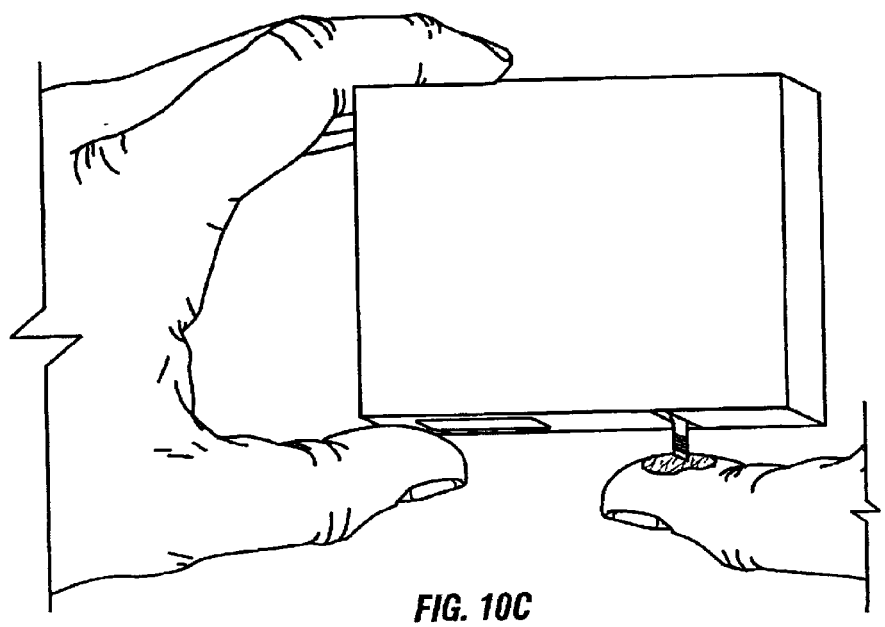

Referring to FIGS. 10A–10C which illustrate the steps of the subject methods in more detail, FIG. 10A illustrates meter 2 being manually grasped and held in a substantially upright position. As shown, a plurality of test strips 62 are positioned adjacent end 6b when the meter is in a substantially upright position. FIG. 10B illustrates meter 2 moved from the substantially upright position shown in FIG. 10A to a substantially upside down position such that the plurality of test strips 62 move towards dispensing end 6a through test strip selecting element 20. Of course, meter 2 may begin in the substantially upside down position such that test strips 62 are already moved into test strip selecting element 20.

When meter 2 is positioned in this manner, i.e., positioned substantially upside down, a single test strip 62a is selected or separated from the rest of the test strips 62 and dispensed. More specifically, the plurality of test strips 62 move into test strip selecting element 20 from test strip area 10, which test strips 62 are then segregated by the frustum-shaped configuration of the test strip selecting element 20, e.g., by a directing element 27 in certain instances. A single test strip 62a is ultimately segregated from plurality 62 and selected by slot 22 so that selected test strip 62a extends through dispensing outlet 5. That is, a plurality of test strips 62 is moved from the interior of housing 1, i.e., from test strip area 10, into second end 23 of test strip selecting element 20 when meter 2 is positioned in a manner which causes the plurality of test strips 62 to move towards dispensing wall or side 6*a*. As the plurality of test strips 62 move towards first end 21 of substantially frustum-shaped cavity 25, the number of test strips gradually decreases due to the funnel-like portion or the tapered walls (and also due to a directing element if present) of substantially frustum-shaped cavity 25 of test strip selecting element 20. Ultimately, a single test strip 62*a* is separated or selected from the remaining test strips 62 due to the continuously reduced cross-sectional area of substantially frustum-shaped cavity 25 and to the configuration of slot 22, where the test strip is selected by slot 22 and ultimately dispensed via dispensing outlet 5. In certain embodiments, meter 2 is gently agitated along the plane defined by −γ to +γ (see FIG. 9C) to facilitate test strip selection. Usually, test strip 62*a* is oriented in dispensing outlet 5 in such a manner that sample may be oriented in dispensing readily applied thereto. Accordingly, test strip 62*a* is typically dispensed for use such that the sample application area of test strip 62*a* is the portion of the test strip that protrudes from meter 2 (see FIG. 10B). Furthermore, the test strip is usually also appropriately positioned in meter 2 such that analyte concentration determination may be made without further positioning of test strip 62*a* in meter 2. For example, contacts on test strip 62*a* mate with contacts of meter 2 so as to couple test strip 62*a* with means for determining analyte concentration 4 of meter 2.

Once a single test strip 62*a* is selected within slot 22 of test strip selecting element 20 and dispensed via dispensing outlet 5, an individual may now use the dispensed test strip 62*a* to determine analyte concentration in a physiological sample. That is, physiological sample, e.g., whole blood, interstitial fluid, etc., to be analyzed is deposited on the sample application area of test strip 62*a*. As described above, the subject invention enables analyte concentration determination without removing dispensed test strip 62*a* from meter 2. Accordingly, meter 2 with test strip 62*a* protruding therefrom is brought into contact with physiological sample, as shown in FIG. 10C, either by moving meter 2 with dispensed test strip in contact with sample or vice versa. Once sample is applied, the concentration of an analyte, e.g., the concentration of glucose in blood, may be determined. As described above, contacting of the sample to the test strip results in a reaction which can be measured either optically or electrochemically. For example, contacting of the blood with the reagents on the test strip results in a reaction in which glucose is oxidized and a mediator is reduced. An electric potential difference is then applied between the working and reference electrodes and the resulting current is measured and related to the amount of glucose present in the sample. Regardless of which type of system, i.e., photometric or electrochemical, the analyte concentration thus determined is typically displayed via display means associated with meter 2, e.g., one or more LED displays and/or one or more LCD displays and/or an audible message or signal.

Figure 13A:
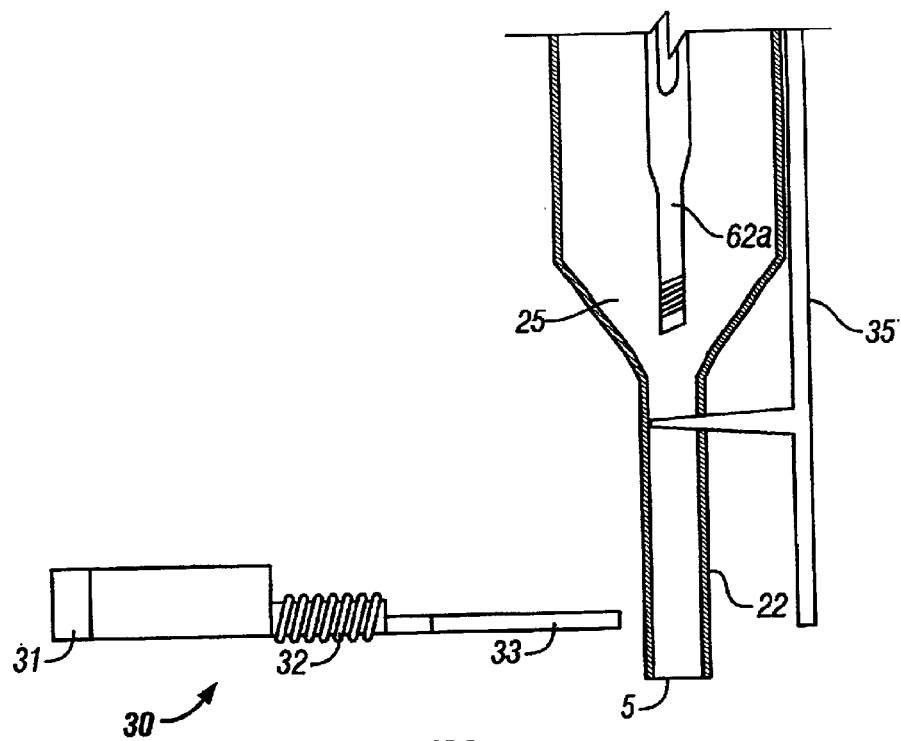
FIGS. 13A–13C illustrates the steps of positioning and securing a test strip in a dispensing outlet of a subject meter so that a sample may be applied to the test strip.
Figure 13B:
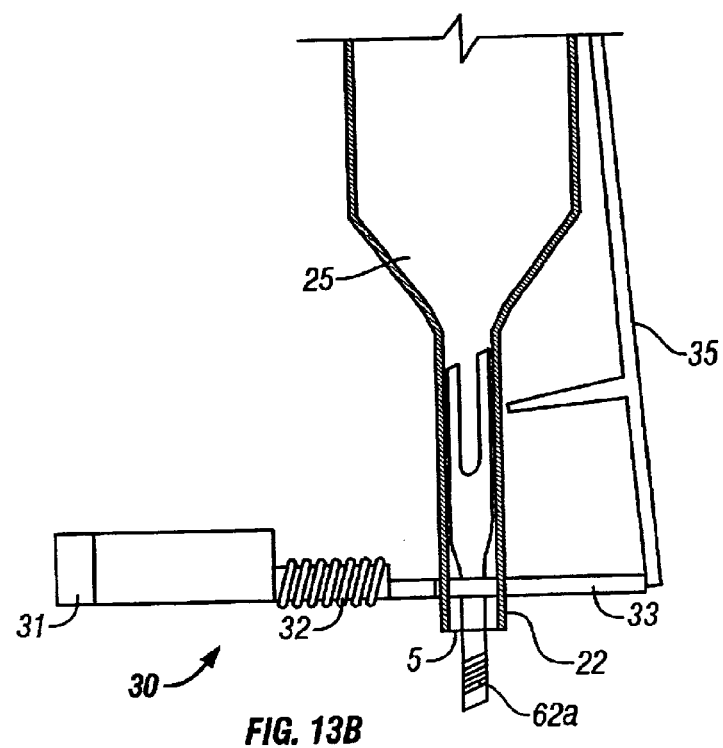
Figure 13C:
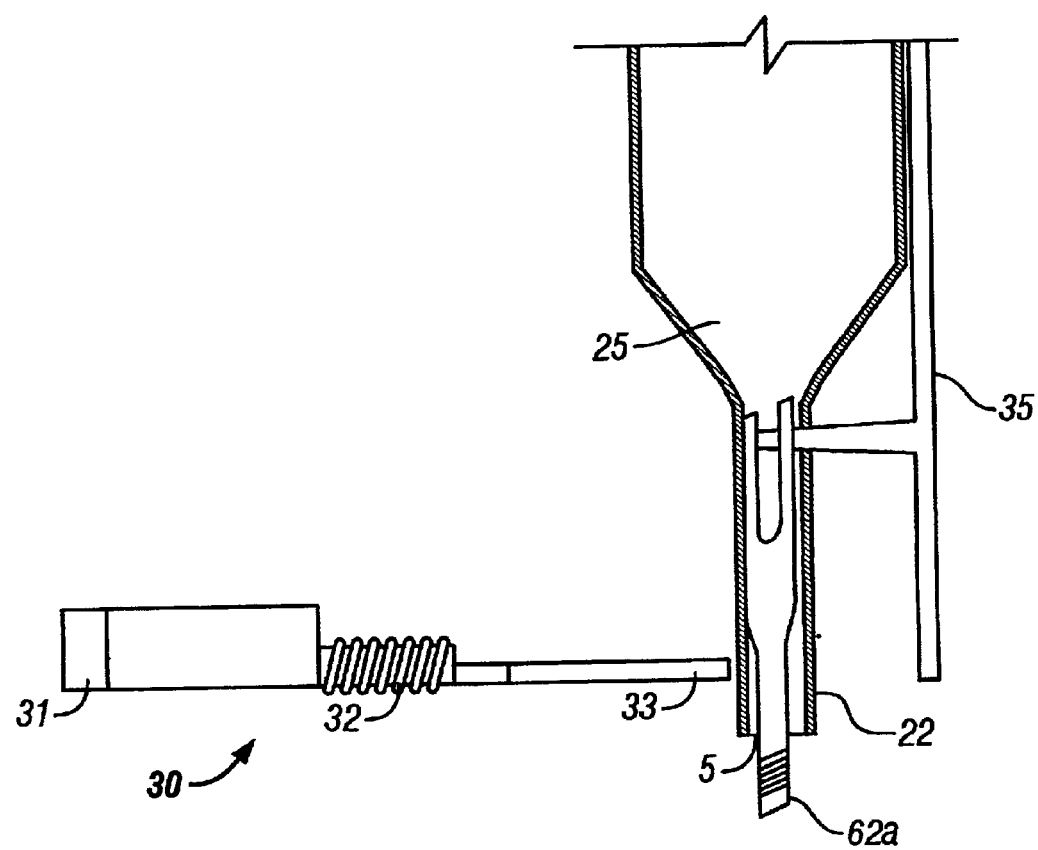

The subject methods also include limiting the movement of a selected test strip and securing the selected test strip in dispensing outlet 5 so that sample may be applied thereto while the meter is in a substantially upside down position. That is, test strip 62*a* is maintained in outlet 5 so that it is prevented from completely falling out of outlet 5. FIGS. 13A–13C illustrate how the test strip movement limiting element 30 and test strip securing element 35, as described above, work together to limit the movement of a selected test strip and secure the test strip 62*a* in outlet 5 of meter 1 so that a sample may be applied thereto while appropriately positioned in outlet 5. That is, test strip movement limiting element 30 and test strip securing element 35 orient and secure a test strip so that it partially protrudes an appropriate distance from the meter such that sample may be applied to the test strip while the test strip is secured in outlet 5 of the meter. Likewise, the test strip is appropriately maintained such that analyte concentration determination may be provided while the test strip is secured in outlet 5, i.e., the test strip is appropriately aligned with means for determining analyte concentration, whether electrochemically or photometrically.

FIG. 13A shows an exploded, side view of a portion of meter 1 showing slot 22 and a portion of cavity 25. Test strip movement limiting element 30 is positioned in a first position whereby the prongs of block 33 are positioned adjacent a wall of slot 22, i.e., the prongs do not perpendicularly traverse slot 22 in this first position. Test strip securing element 35 is positioned in a first position such that a portion thereof protrudes through an opening in slot 22, such that it obstructs the interior of slot 22.

When meter 2 is turned substantially upside down, as described above, trigger mechanism 31, which is operatively associated with spring loaded actuator 32, is depressed by the user. As shown in FIG. 13B, test strip movement limiting element 30 moves to a second position by the depression of trigger mechanism 1 such that actuator 32 drives block 33 perpendicularly through an opening in slot 22 such that the prongs of block 33 partially obstruct the interior of slot 22. In this manner, a test strip that is entering slot 22 will engage the prongs of block 33. The prongs also engage test strip securing device 35 and deflect it from its first position. As such, test strip securing element 35 is moved to a second position by the engagement with block 33 such that test strip securing element is deflected by the force of block 33 and is driven or moved out of the interior of slot 22. In this manner, a passageway for a test strip is provided in slot 22, through the prongs of block 33.

Accordingly, when test strip 62*a* is selected in slot 22, it engages block 35 such that a portion having a diameter less than the area between the prongs, e.g., the sample application portion, of test strip 62*a* moves through the prongs of block 33 and becomes positioned above the prongs of block 35, such that a portion of the test strip that is able to move passed block 33 extends through outlet 5, while the remaining portion of test strip 62*a* is prevented from moving beyond block 35. As such, test strip 62*a* is prevented from further travel and protrudes a predetermined or set distance from outlet 5.

Upon release of trigger mechanism 31, as shown in FIG. 13C, test strip movement limiting element 30 moves back to a first position such that actuator 32 releases block 33 which then moves out of the interior of slot 22 and test strip securing element 35, no longer deflected by test strip movement limiting element 30, moves back to a first position whereby it protrudes into the interior of slot 22 to engage test strip 62*a* and secure the test strip in the position it assumed by the interaction with test strip movement limiting element 30. As test strip 62*a* is now secured in an appropriate position in slot 22 and outlet 5, i.e., positioned by the interaction with test strip movement limiting element 30, test strip securing element 35 securely holds test strip 62*a* in the dispensed position such that test strip 62*a* does not completely fall out of outlet 5 when meter 1 is substantially upside down and is instead secured in a position such that a portion protrudes from outlet 5 and a portion remains in the interior of meter 1. As described above, usually the portion of test strip 62a that extends beyond outlet 5 is the portion where sample is applied.

In certain embodiments where the subject meter is configured as an electrochemical meter, test strip movement limiting element 30 actuates the electrical connections with the test strip when the test strip movement limiting element 30 is in a second position, i.e., test strip securing element 35 includes one or more electrical contact member(s) (not shown) which connect with the contact member(s) on the test strip to provide an electrical connection therewith.

Once testing is completed, test strip 62a may be physically removed from meter 2 by the user by grasping the edges thereof and gently pulling test strip 62a in a direction away from meter 1.

Kits

Finally, kits for practicing the subject methods are provided. The subject kits at least include one or more test strip dispensing devices of the subject invention. Oftentimes, a plurality of subject devices is included. The subject kits may also include one or more test strips, usually a plurality of test strips. The subject kits may further include an element for obtaining a physiological sample. For example, where the physiological sample is blood, the subject kits may further include an element for obtaining a blood sample, such as a lance for sticking a finger, a lance actuation means, and the like. In addition, the subject kits may include a control solution or standard, e.g., a control solution that has a known analyte concentration such as a known glucose concentration. The kits may further include instructions for using the subject devices for selecting and dispensing a test strip and may also include instruction for loading the subject meters with test strips and/or for determining the presence and/or concentration of at least one analyte in a physiological sample applied to a test strip. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description and discussion that the above described invention provides a simple, quick and convenient way to dispense test strips. The above described invention provides a number of advantages, including, but not limited to, ease and low cost manufacture, minimal components, portability, ease of use, particularly for visually and dextrally impaired individuals, and minimal test strip damage from contaminants from an individual's hands. As such, the subject invention represents a significant contribution to the art.

The subject invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

The specific devices and methods disclosed are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. A device for selecting and dispensing a single test strip at a time and determining the concentration of an analyte in a physiological sample applied to the dispensed test strip, said device comprising:
    (a) an internal structure comprising a test strip selecting element comprising a continuously reduced cross-sectional area configured to select a single test strip at a time; and
    (b) means for determining the concentration of an analyte in a physiological sample applied to the selected test strip.

2. The device according to claim 1, wherein said continuously reduced cross-sectional area is a substantially frustum-shaped cavity.

3. The device according to claim 2, wherein said substantially frustum-shaped cavity has a cross sectional shape selected from the group consisting of rectangular, square, circular and elliptical.

4. The device according to claim 1, wherein said test strip selecting element comprises a test strip selecting slot.

5. The device according to claim 4, wherein said device further includes a dispensing outlet and said test strip selecting slot is in communication with said dispensing outlet.

6. The device according to claim 4, wherein said test strip selecting slot is configured to be permissive of only one test strip at a time.

7. The device according to claim 1, further comprising a test strip movement limiting element for limiting the movement of the single test strip.

8. The device according to claim 7, wherein said test strip movement limiting element is spring loaded.

9. The device according to claim 7, wherein said test strip movement limiting element is configured to move from a first position to a second position, whereby said second position blocks a portion of the single test strip from further movement.

10. The device according to claim 1, further comprising a test strip securing element for securing the test strip in a fixed position.

11. The device according to claim 10, wherein said test strip securing element is configured to be deflected from a first position to a second position, whereby said second position engages and secures the single test strip.

12. The device according to claim 10, wherein said test strip securing element comprises electrical contacts.

13. The device according to claim 1, wherein said test strip selecting element further comprises a directing element for directing the single test strip through said continuously reduced cross-section diameter.

14. The device according to claim 13, wherein said directing element comprises a series of steps.

15. The device according to claim 1, wherein the analyte is glucose.

16. A method for containing at least one test strip and for dispensing a single test strip at a time from a meter, said method comprising:
    (a) providing a meter, wherein said meter has at least one test strip contained therein,
    (b) positioning said meter with respect to the ground to cause said single test strip to move from a contained position to a dispensed position, whereby a single test strip is dispensed from said meter at a time.

17. The method according to claim 16, wherein said step of positioning comprises placing said meter in a substantially upside down position.

18. The method according to claim 17, wherein said substantially upside down position comprises an angle that ranges from about −20° to about +20° relative to the central axis of said meter when said central axis of said meter is positioned perpendicular to the ground and the top side of said meter is closer to said ground than the bottom side of said meter is positioned with respect to said ground.

19. The method according to claim 16, wherein said meter comprises an area having a continuously reduced cross-section, wherein said step of positioning comprises moving said single test strip through said area.

20. The method according to claim 19, wherein said area is a substantially frustum-shaped cavity.

21. The method according to claim 16, wherein a plurality of test strips is contained in said meter.

22. The method according to claim 16, further comprising coupling a test strip container to said meter so as to provide a passageway therebetween, whereby said at least one test strip is moved from said coupled test strip container to said meter through said passageway.

23. The method according to claim 16, further comprising limiting the movement of said single test strip so that a portion of said single test strip extends beyond the exterior of said meter and a portion remains inside said meter when said test strip is in said dispensed position.

24. The method according to claim 16, further comprising securing said single test strip in said dispensed position.

25. The method according to claim 16, further comprising applying physiological sample to said dispensed test strip.

26. The method according to claim 25, further comprising determining the concentration of an analyte in said physiological sample.

27. The method according to claim 26, wherein said analyte is glucose.

28. The method according to claim 26, wherein said analyte concentration determination is accomplished optically or electrochemically.

29. A method for containing at least one test strip and for dispensing a single test strip at a time from a meter, said method comprising:

(a) providing a meter having an internal structure comprising a test strip selecting element comprising a continuously reduced cross-sectional area configured to select a single test strip at a time, wherein said meter has at least one test strip contained therein;

(b) positioning said meter with respect to the ground to cause said single test strip to move from a contained position to a dispensed position, whereby a single test strip is dispensed from said meter at a time.

30. A kit for containing at least one test strip and dispensing a single test strip at a time, said kit comprising:

(a) at least one device according to claim 1; and (b) at least one test strip.

31. The kit according to claim 30, wherein said at least one test strip is an electrochemical test strip.

32. The kit according to claim 30, wherein said at least one test strip is a calorimetric test strip.

33. The kit according to claim 30, further comprising a plurality of test strips.

34. The kit according to claim 30, further comprising an element for obtaining a physiological sample.

35. The kit according to claim 30, further comprising control solution.

* * * * *